(12) United States Patent
Parks et al.

(10) Patent No.: US 8,790,275 B2
(45) Date of Patent: Jul. 29, 2014

(54) ANALYSIS AND VISUALIZATION METHODS USING MANOMETRY DATA

(75) Inventors: Thomas R. Parks, Hermosa Beach, CA (US); Ray E. Clouse, St. Louis, MO (US)

(73) Assignee: Given Imaging (Los Angeles) LLC, Yogneam (IL)

(*) Notice: Subject to any disclaimer, the term of this patent is extended or adjusted under 35 U.S.C. 154(b) by 1930 days.

(21) Appl. No.: 11/129,030

(22) Filed: May 13, 2005

(65) Prior Publication Data

US 2006/0004304 A1 Jan. 5, 2006

Related U.S. Application Data

(60) Provisional application No. 60/571,815, filed on May 17, 2004.

(51) Int. Cl.
| | | |
|---|---|---|
| *A61B 5/00* | (2006.01) | |
| *A61B 5/03* | (2006.01) | |
| A61B 5/145 | (2006.01) | |
| A61B 5/01 | (2006.01) | |
| A61B 5/053 | (2006.01) | |

(52) U.S. Cl.
CPC ......... *A61B 5/037* (2013.01); *A61B 2562/0247* (2013.01); *A61B 2562/043* (2013.01); *A61B 5/145* (2013.01); *A61B 5/01* (2013.01); *A61B 5/053* (2013.01)
USPC ...................................................... 600/561

(58) Field of Classification Search
USPC ......... 600/595, 546, 559, 407, 558, 561, 557; 607/40
See application file for complete search history.

(56) References Cited

U.S. PATENT DOCUMENTS

| 5,533,515 | A | 7/1996 | Coller et al. | |
|---|---|---|---|---|
| 6,165,142 | A * | 12/2000 | Bar | 600/595 |
| 7,378,856 | B2 | 5/2008 | Peine | |
| 7,476,204 | B2 | 1/2009 | Parks et al. | |
| 2003/0135120 | A1 * | 7/2003 | Parks et al. | 600/463 |

OTHER PUBLICATIONS

Medical Measurement Systems, Release Notes 1996, 1 page.
Abstract for "Changes in upper esophageal motor function in reflux esophagitis by high resolution manometry (HRM)," Supplement to Gastroenterology, Digestive Disease Week and the $102^{nd}$ Annual Meeting of the Amer. Gastroenterological Assoc., Apr. 2001, p. A-219, #1151, vol. 120, No. 5, Suppl. 1.
Abstract for "Pressure-geometry relationships in the stomach analyzed through computer simulation," *Gastroenterology*, Digestive Disease Week and the $100^{th}$ Annual Meeting of the Amer. Gastroenterological Assoc., May 16-19, 1999, Orlando, FL, vol. 116, No. 4, Part 2, #G4594.

(Continued)

*Primary Examiner* — Jeffrey G Hoekstra
*Assistant Examiner* — Fangemonique Smith
(74) *Attorney, Agent, or Firm* — Wolf, Greenfield & Sacks, P.C.

(57) ABSTRACT

A system and methods that provide for visualization and/or characterization of manometry data. Visual representations of pressure information represent pressure information measured over time by sensors positioned within an organism. Markers may be provided on the visual representations. Using the system and methods described herein, various characteristics of an organism and/or events that occur within the organism may be determined.

51 Claims, 19 Drawing Sheets

(56) References Cited

OTHER PUBLICATIONS

Abstract for "Technical Aspects of high resolution perfusion manometry—An underwater zero improves accuracy of measurement of catheter offset and transducer drift," Supplement to Gastroenterology, Digestive Disease Week and the 97th Annual Meeting of the Amer. Gastroenterological Assoc., May 11-14, 1997, Washington, DC, p. A745, vol. 112, No. 4.

Abstract for "Insights into stomach mechanics from concurrent gastric ultrasound and manometry," *Gastroenterology*, Official Journal of the Amer. Gastroenterological Assoc., Oct. 1994, p. 1236, vol. 107, No. 4.

Abstract for "Does high resolution manometry detect esophageal motility disorders more reliable than conventional manometry?" *Dysophagia*, An International Multidisciplinary Journal Devoted to Swallowing and its Disorders, Official Journal of the Dysphgia Research Society, p. 146, vol. 16, No. 1, Winter 2001.

R. E. Clouse, M.D., et al., "Topographic esophageal manometry: An emerging clinical and investigative approach," *Digestive Diseases*, pp. 64-74, 2000, vol. 18.

P. J. Kahrilas et al., Effect of peristaltic dysfunction on esophageal volume clearance, *American Gastroenterological Assoc.* 1988, pp. 73-80, vol. 94.

R. E. Clouse, M.D., et al., "Application of topographical methods to clinical esophageal manometry," *Am. J. of Gastroenterology*, Nov. 2000, pp. 2720-2730, vol. 95, No. 10.

R. E. Clouse and A. Staiano, "Topography of the esophageal peristaltic pressure wave," *Amer. Physiological Society*, 1991, pp. G677-G684.

G. S. Hebbard, TRACE! 1.1, *User Manual, Advanced Manometry Systems*, Adelaide, Aug. 2001, 182 pages.

Meijing Li et al., "Analyses of Normal and Abnormal Esophageal Transport Using Computer Simulations", *The American Physiological Society*, pp. G525-G543, dated Aug. 2, 1992.

Thompson, Patty "Clouse Contour and Axial Transformation Plotting", *Medical Measurement Systems*, p. 1, dated Jul. 11, 1997.

Lewis, John "Esophageal Manometry Report", *Medical Measurement Systems*, p. 1, dated May 11, 1997.

"Esophageal Contour Plots—Swallow Simulation", *Medical Measurement Systems*, pp. 1-5, dated Nov. 1997.

Geoff Hebbard, Computerised Mapping Provides New Insights Into Oesophaegeal Motility Disorders, Repatriation General Hospital, Daw Park, 14 IMS Slides.

Geoff Hebbard, Current Investigations—A Waste of Time?, *Repatriation General Hospital*, Daw Park, 14 IMS Slides.

Geoff Hebbard, Spatiotemporal Pressure Maps In Vivo, *Repatriation General Hospital*, Adelaide, Australia, 14 IMS Slides.

\* cited by examiner

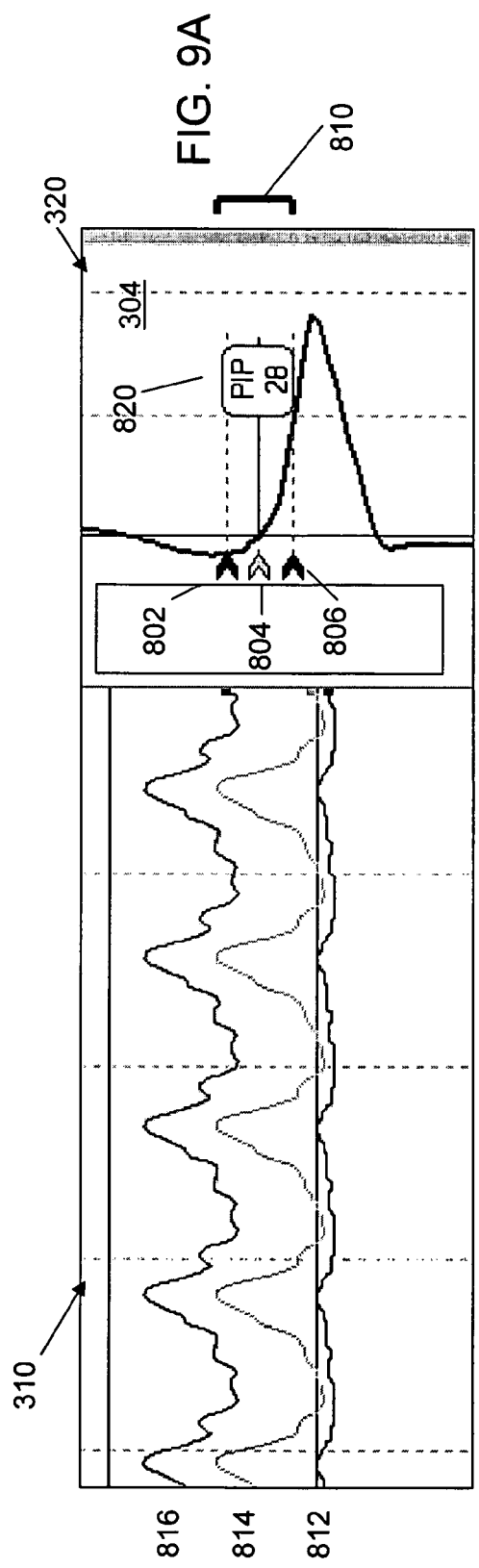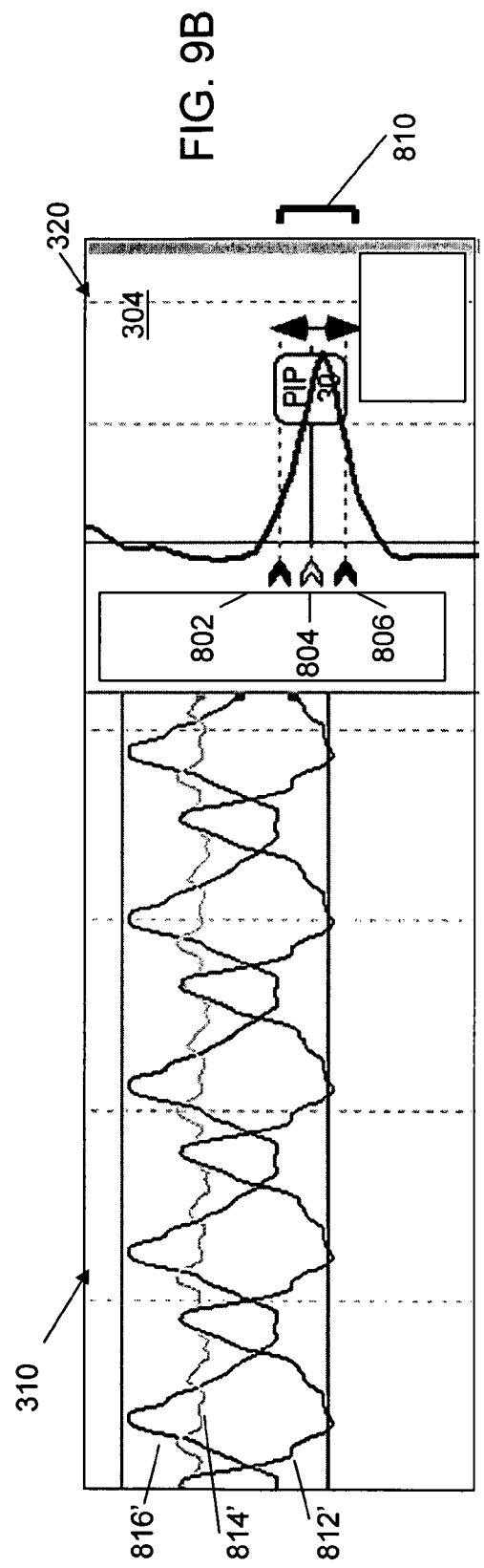

ANALYSIS AND VISUALIZATION METHODS USING MANOMETRY DATA

RELATED APPLICATIONS

This application claims benefit under 35 U.S.C. §119(e) to U.S. Provisional Application Ser. No. 60/571,815, entitled "ANALYSIS AND VISUALIZATION METHODS USING HIGH RESOLUTION MANOMETRY DATA" filed on May 17, 2004, which is herein incorporated by reference in its entirety.

GOVERNMENT RIGHTS

The U.S. Government may have rights to one or more aspects of the invention set forth herein.

BACKGROUND OF INVENTION

The esophagus is a tubular organ that carries food and liquid from the throat to the stomach. It contains muscles that rhythmically contract whenever a person swallows. This contraction generally occurs as a sweeping wave carrying food down the esophagus to the stomach. This sweeping wave of contraction is typically referred to as peristalsis. An upper esophageal sphincter (UES) is located at an upper end of the esophagus. The UES is a muscle that serves as a valve between the esophagus and the pharynx from which the esophagus receives food and liquid when swallowing.

The lower esophageal sphincter (LES) is located at a lower end of the esophagus. The LES is a muscle that serves as a valve between the esophagus and the stomach. The LES protects the lower esophagus from stomach acid and bile, which causes the discomfort of heartburn and in time, can damage or scar the esophagus.

The diaphragm is a muscular membrane that assists is respiration and intersects the upper Gastrointestinal (GI) tract at an approximate right angle, typically within the length of the LES, creating a pressure inversion point (PIP), which is often referred to as the respiratory inversion point (RIP). As used herein, an "upper GI tract" includes at least the UES, esophagus, LES and at least portions of the pharynx and stomach. The PIP is named as such because it is a point along the length of the upper GI tract (typically within, but sometimes distal to, the LES) where the pressure associated with respiration inverts. Above the PIP, pressure decreases during inhalation and increases during exhalation. In contrast, below the PIP, the pressure increases during inhalation and decreases during exhalation. A hiatal hernia occurs if the PIP (i.e., the intersection of the diaphragm and the LES) is not within the LES, but is located below the LES within the upper regions of the stomach.

Manometry is the measurement of pressure. Esophageal manometry measures the muscular pressure exerted along the upper GI tract, for example, during peristalsis. Esophageal manometry is used to evaluate the contraction function of the upper GI tract in many situations (e.g., breathing, swallowing food, swallowing liquid, drinking, coughing, etc.) and can be useful for diagnosing symptoms that originate in the esophagus, for example, difficulty in swallowing food or liquid, heartburn, and chest pain to determine the cause of the symptoms, for example, dysphasia or achalasia.

A variety of esophageal manometry systems have been used to study pressure along the upper GI tract. Such systems typically include a probe that is inserted into the upper GI tract and one or more pressure sensors that detect pressure from different positions within the upper GI tract. One type of a probe is a catheter. An esophageal manometry system that has a catheter as a probe is a referred to herein as a catheter-based esophageal manometry system. Types of catheter-based esophageal manometry systems include solid state systems and water perfuse systems. In water perfuse systems, pressure sensors are located external to the catheter. Each pressure sensor has a corresponding tube that extends into the catheter and pumps fluid (e.g., water) at some longitudinal position of the catheter against the interior surfaces of the GI tract. The pressure resulting from the impact of the fluid against the interior surface is transmitted via the fluid through the tube to the pressure sensor, where it is detected. In contrast, solid state systems do not use fluids, and each sensing element is attached to or embedded within the catheter and detects pressure locally at the point of impact with the interior surface of the upper GI tract. Each sensor transmits its detected values out of the catheter using an electronic or optical signal.

An esophageal manometry system may include or be accompanied by an application (e.g., software, firmware, hardware or a suitable combination thereof) that visually indicates the values detected by the sensors to a user, and may be capable of visually indicating the values detected by the sensor on a temporal representation in real time using a line trace. As used herein, a "temporal representation" is a plot having a temporal dimension representing time, on which values detected over time are visually indicated, concurrently, at temporal positions along the temporal dimension, each detected value visually indicated at a temporal location corresponding to a time at which the value was detected. A temporal representation is useful to concurrently illustrate values of a physical property detected at one or more positions over time.

As used herein, a "line trace" is a visual representation that visually indicates values detected over time at a location on a temporal plot having a temporal dimension corresponding to time. For each location, a baseline for the location running parallel to the temporal dimension is indicated. The value detected at the corresponding position within the region at each time is represented as an offset from the baseline at a temporal location along the temporal dimension that corresponds to the time. The amount of the offset corresponds to the detected value. Each visually indicated value detected at the position may be connected by a continuous line, which, depending on the detected values, may be a straight line or a curved line.

As used herein, a "contour plot" is a visual representation that visually indicates values detected over time at locations on a temporal plot having a temporal dimension corresponding to time and a spatial dimension corresponding to a region. A contour plot may represent to a user pressure data derived from pressure information measured by sensors at a plurality of positions over time. A contour plot may include one or more tones which each represent a pressure range.

SUMMARY OF INVENTION

In one aspect, the invention relates to a method of processing pressure data including a plurality of pressure values indicative of pressure information measured by a plurality of sensors within a sphincter region of an organism during a first time. The pressure data is received. A maximum pressure value of the region for the first time is determined from the pressure data.

In another aspect, the invention relates to a method of visually representing pressure data measured over time by a plurality of sensors positioned within an organism. A first display representing a first region within the organism is provided. A movable set of markers is provided in the first display. Each marker of the movable set of markers represents a respective position within the first region. The movable set of markers is movable along a spatial dimension within the first display representing the first region. For each marker of the movable set of markers, a visual representation of values corresponding to pressure information measured over time at the respective position within the first region represented by the marker is provided. The visual representation of values is provided in a second display concurrently to providing the first display.

In yet another aspect, the invention relates to a method of locating a region of interest within an organism using visual representations of pressure information measured by a plurality of sensors positioned within the organism. A first display representing a first region within the organism is viewed. The first display includes a movable set of markers. Each marker of the movable set of markers represents a respective position within the first region. The movable set of markers are movable along a spatial dimension within the first display representing the first region. A second display displayed concurrently to the first display is viewed. For each marker of the movable set of markers, a visual representation of values corresponding to pressure information measured over time at the respective position within the first region represented by the marker is provided. The position of the region of interest within the organism is determined based on the viewing of the first and second displays.

In yet another aspect, the invention relates to a method of visually representing pressure information measured during a temporal interval by a plurality of sensors positioned within a region of an organism, each sensor positioned at a respective position within the region. A temporal representation is provided on which the pressure information is visually represented at least partially based on the pressure information. The temporal representation has a temporal dimension representing time and a spatial dimension representing the region. The temporal representation comprises a first location along the spatial dimension corresponding to a first position within the region. A first set of markers is provided on the temporal representation. The first set of markers corresponds to the first position within the region and defines a first sub-interval of the temporal interval. The first sub-interval corresponds to an event represented by the pressure information.

In a further aspect, the invention relates to a method of visually representing pressure information measured during a first temporal interval by a plurality of sensors positioned at respective positions within a region of an organism. A first visual representation of the pressure information is provided in a temporal display. The temporal display has a temporal dimension representing time and a spatial dimension representing the region. A temporal control movable along the temporal dimension is provided in the first display. A first location of the temporal control along the temporal dimension indicates a first time during the temporal interval. A second visual representation of pressure information measured by the plurality of sensors at the first time indicated by the temporal control is provided in a second display. The second display is provided concurrently to the first visual representation being provided.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 9A and 9B are portions of screenshots illustrating examples of line traces and corresponding markers;

DETAILED DESCRIPTION

A manometric analysis and visualization system for visualizing high resolution manometry data in real time is described in co-pending application Ser. No. 10/281,068, filed on Oct. 24, 2002, and titled "VISUALIZATION OF VALUES OF A PHYSICAL PROPERTY DETECTED IN AN ORGANISM OVER TIME" by Tom R. Parks (hereinafter, the Parks application) which is herein incorporated by reference in its entirety.

Although aspects of the invention described below are described primarily in relation to visually indicating values of physical properties (e.g., pressure, pH level, temperature, voltage, tissue impedance) detected from an organism (e.g., a human), or values derived therefrom, over time, such aspects are not limited thereto, but apply to visually indicating any types of values over time. Further, although aspects of the invention described below are described primarily in relation to visually indicating values of physical properties detected within the upper GI tract, such aspects are not limited thereto, but apply to visually indicating physical properties detected within other organs or combinations of organs, including tubular organs, located within an organism such as, for example, the duodenum, small bowel, bile duct, colon, Sphincter of Oddi, anus or rectum. Further, such values may be detected along a spatial dimension external to an organism, for example, on an exterior surface of an organism.

Embodiments of the invention may employ systems and methods including visualization techniques, described in co-pending U.S. patent application Ser. No. 11/596,837 (published as US2009/0024001) titled "MANOMETRY PROBE AND DATA VISUALIZATION" by Tom Parks, filed on May 13, 2005 as PCT application (PCT/US2005/016809), which is hereby incorporated by reference in its entirety.

The function and advantage of these and other embodiments of the present invention will be more fully understood from the examples described below. The following examples are intended to facilitate an understanding of aspects of the present invention and their benefits, but do not exemplify the full scope of the invention.

Figure 1A:
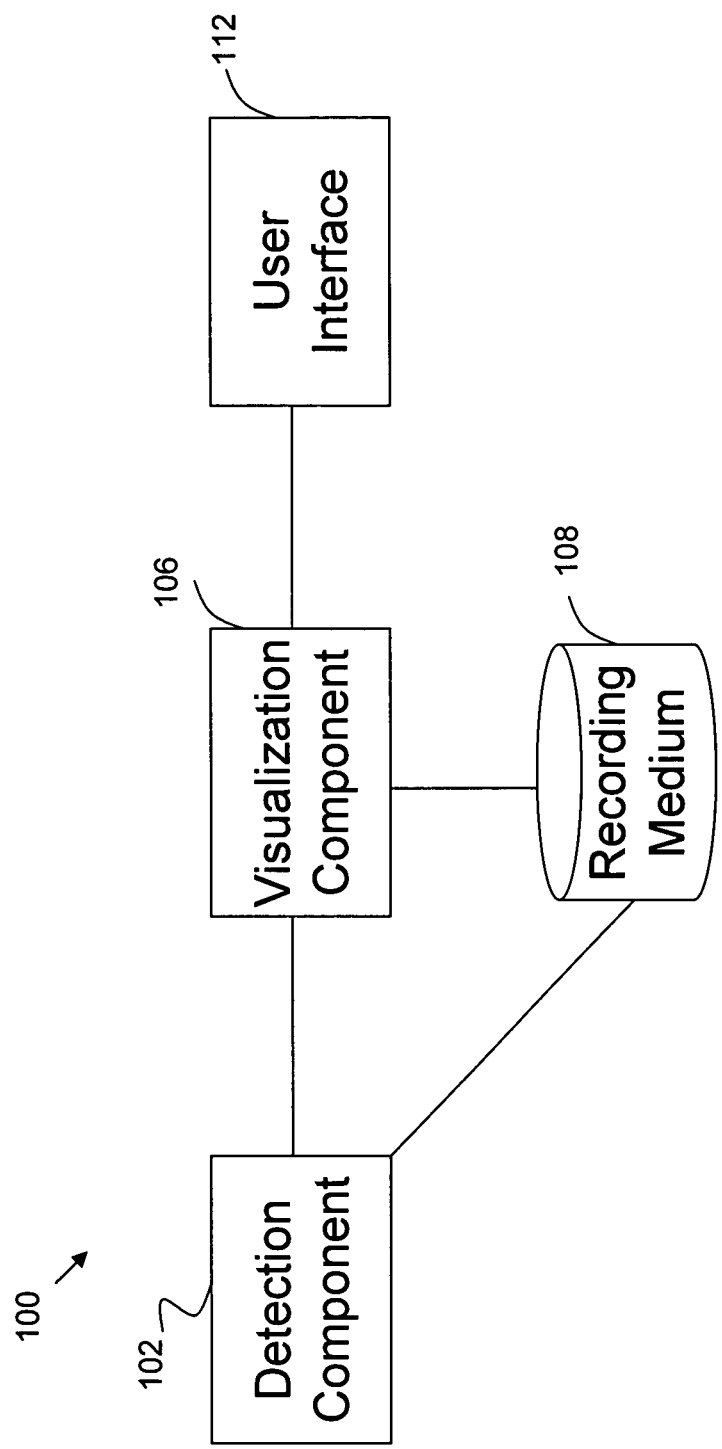
FIG. 1A is a block diagram illustrating an example of a system for providing representations of pressure data to a user.

FIG. 1A is a block diagram illustrating an example of a system 100 for visually indicating values detected (e.g., within an organism) over a period of time to a user. System 100 may include any of a detection component 102, a visualization component 106, a recording medium 108, a user interface 112, other components or any suitable combination of the foregoing.

As used herein, a "user interface" is an application or part of an application (i.e., a set of computer-readable instructions) that enables a user to interface with an application during execution of the application. A user interface may include code defining how an application outputs information to a user during execution of the application, for example, visually through a computer screen or other means, audibly through a speaker of other means, and manually through a game controller or other means. Such user interface also may include code defining how a user may input information during execution of the application, for example, audibly using a microphone or manually using a keyboard, mouse, game controller, track ball, touch screen or other means.

The user interface 112 may define how information is visually presented (i.e., displayed) to the user, and defines how the user can navigate the visual presentation (i.e., display) of information and input information in the context of the visual presentation. During execution of the application, the user interface may control the visual presentation of information and enable the user to navigate the visual presentation and enter information in the context of the visual presentation. Types of user interfaces range from command-driven interfaces, where users type commands, menu-driven interfaces, where users select information from menus, and combinations thereof, to GUIs, which typically take more advantage of a computer's graphics capabilities, are more flexible, intuitive and easy to navigate and have a more appealing "look-and-feel" than command-driven and menu-driven visual user interfaces. As used herein, the visual presentation of information presented by a user interface or GUI is referred to as a "user interface display" or a "GUI display", respectively.

The detection component 102 may detect pressure information of an organism (e.g., from within an organism) over a period of time and provide pressure data including pressure values representing the pressure information to a visualization component 106 and/or a recording medium 108. For example, as will be described in more detail below, if the pressure information is to be visually indicated in real time, then the pressure information is provided to at least the visualization component 106 and also may be persisted in a recording medium 108. If the pressure information is not to be visually indicated in real time, but is to be visually indicated post hoc at a later point in time, then the detection component 102 may provide the pressure data to the recording medium 108 but not to the visualization component 106.

Visualization component 106 may be operable to receive pressure data from detection component 102 (e.g., for real time visual indication) and from recording medium 108 (e.g., for post hoc visual indication). Further, the visualization component may be operable to send data to be persisted to the recording medium during or after visually indicating information to a user. Such information may include the pressure values themselves, display information such as values for display parameters, locations of anatomical landmarks, locations of a probe (e.g., catheter) with respect to an organism, interpolated values, etc. The visualization component 106 also may be operable to receive user input from user interface 112, which may be originated from any of a variety of user input devices (e.g., any of those described above). The visualization component 106 may include any of a variety of logic for generating data to send to the user interface 112 based on the pressure data and received user input.

Figure 1B:
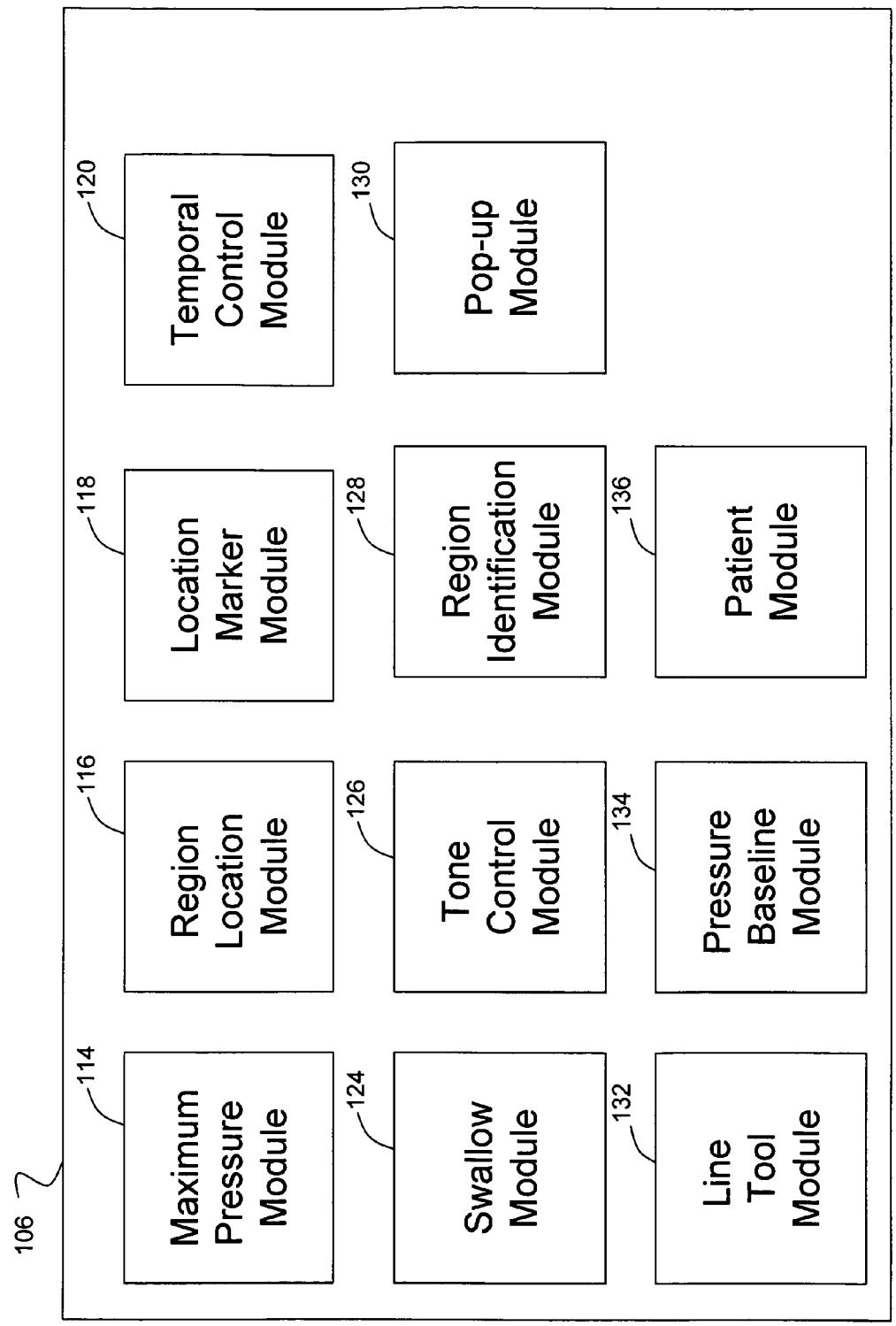
FIG. 1B is a block diagram illustrating an example of a visualization component of the system.

FIG. 1B is a block diagram of visualization component 106. Visualization component 106 may be configured to perform operations on the pressure data, provide for displaying representation(s) of the pressure information and/or perform other operations.

Visualization component 106 may include a maximum pressure module 114 configured to process sphincter pressure data to determine one or more maximum sphincter pressure values. For example, maximum pressure module 114 may be configured to perform one or more acts of a method 700 described in further detail below.

Visualization component 106 may include a region location module 116 configured to display markers and temporal representations for locating a region. For example, region location module 116 may be configured to perform one or more acts of methods 900 and/or 1000 described in further detail below.

Visualization component 106 may include a location marker module 118 configured to display a temporal representation and markers on a temporal representation. For example, location marker module 118 may be configured to perform one or more acts of a method 1300 described in further detail below.

Visualization component 106 may include a temporal control module 120 configured to display a temporal representation and a movable temporal control. For example, temporal control module 120 may be configured to perform one or more acts of a method 1600 described in further detail below.

Visualization component 106 may include a swallow module 124 configured to process pressure data to determine whether a voluntary swallow has occurred. Methods of determining whether a voluntary swallow has occurred are discussed below.

Visualization component 106 may include a tone control module 126 configured to control tone ranges on a temporal representation (e.g., a contour plot). Methods of controlling the tone are discussed below.

Visualization component 106 may include a region identification module 128 configured to process pressure data to identify a position of a region within an organism. Methods of identifying a sphincter are discussed below.

Visualization component 106 may include a pop-up module 130 configured to display a temporal representation in a sub-display. Methods of providing the temporal representation in the sub-display are discussed below.

Visualization component 106 may include a line tool module 132 configured to display a temporal representation and a line tool on the temporal representation for determining characteristics of an event (e.g., a swallow). Methods of determining characteristics of an event are discussed below.

Visualization component 106 may include a pressure baseline module 134 configured to provide for the graphical selection of a location for evaluation of the corresponding gastric or esophageal baseline pressures. Methods of evaluating of pressure data using gastric or esophageal baseline pressures are discussed below.

Visualization component 106 may include a patient module 136 configured to provide for user-controlled display of motor function events using patient-collected data. Methods of providing for user-controlled display of motor function are discussed below.

System 100 and components thereof (e.g., visualization component 106) may be implemented using any of a variety of technologies, including software (e.g., C, C#, C++, Java, or a combination thereof), hardware (e.g., one or more application-specific integrated circuits), firmware (e.g., electrically-programmed memory) or any combination thereof. One or more of the components of system 100 may reside on a single device (e.g., a computer), or one or more components may reside on separate, discrete devices. Further, each component may be distributed across multiple devices, and one or more of the devices may be interconnected.

Further, on each of the one or more devices that include one or more components of system 100, each of the components may reside in one or more locations on the system. For example, different portions of the components of these systems may reside in different areas of memory (e.g., RAM, ROM, disk, etc.) on the device. Each of such one or more devices may include, among other components, a plurality of known components such as one or more processors, a memory system, a disk storage system, one or more network interfaces, and one or more busses or other internal communication links interconnecting the various components. System 100, and components thereof, may be implemented using a computer system such as that described below in relation to FIGS. 17 and 18.

Figure 2:
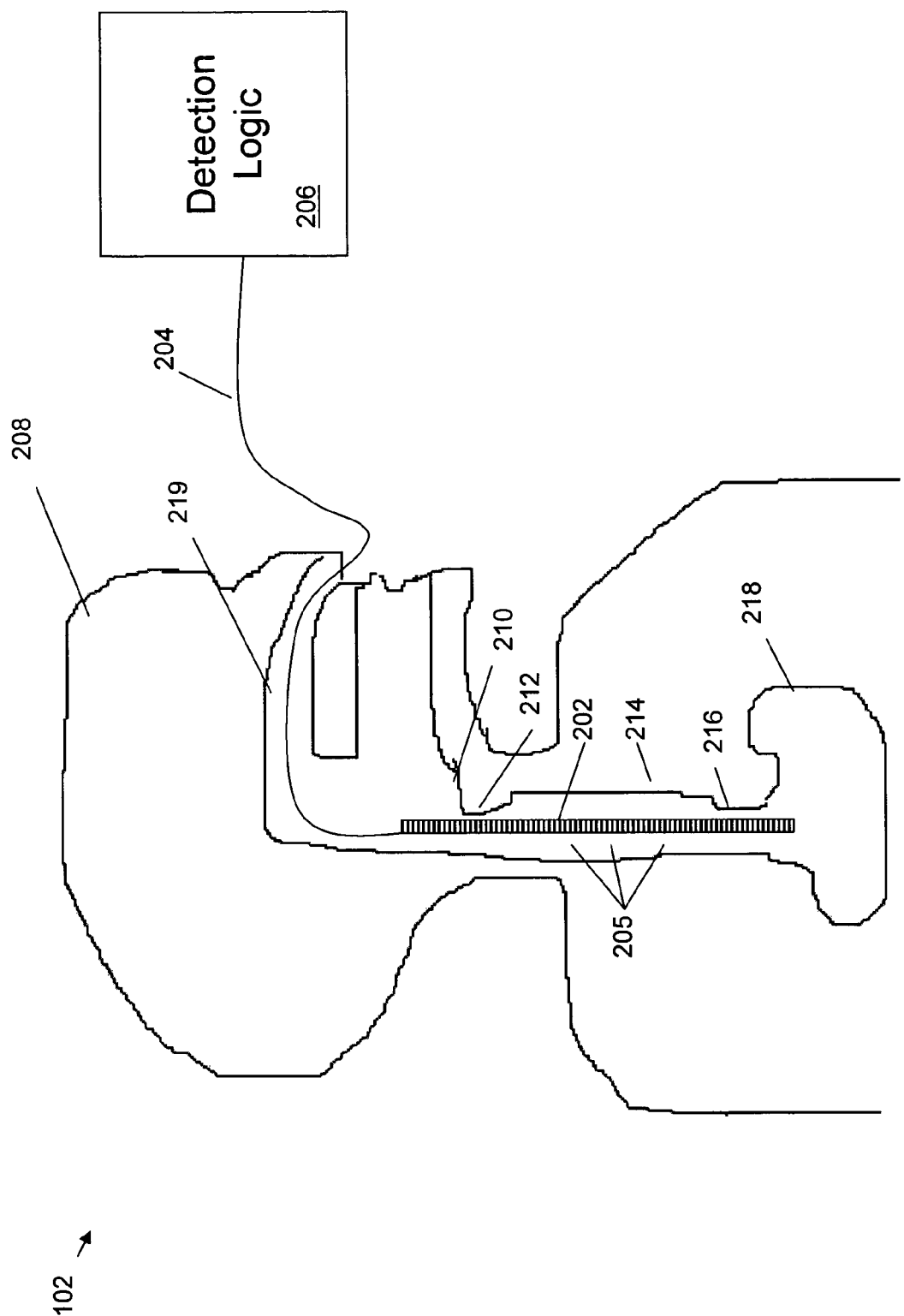
FIG. 2 is a sketch illustrating the esophageal tract in the human body and an example of a detection component for providing esophageal manometry data.

FIG. 2 is a sketch illustrating an example of a detection component 102. The detection component 102 may include any of detection logic 206, transmission medium 204, a plurality of sensors 205 and a probe (e.g., catheter) 202 to which the sensors 205 may be attached or in which the sensors 205 may be embedded. The sensors 205 may be any of a variety of types of sensors, for example, pressure sensors such as a capacitive pressure sensors. For example, sensors 205 may be an array of sensors as described in Patent Cooperation Treaty application Ser. No. 10/493,459 titled "Array Sensor Electronics" by Son et al., published on Mar. 31, 2005 (hereinafter the Son PCT application). Such pressure sensors may be capable of detecting pressure in response to contact with tissue of an organism.

The transmission medium 204 may be any of a plurality of types of transmission media, such as a group of wires (e.g., a bus), a wire, a cable, an optical fiber, a group of optical fibers or a wireless transmission medium (e.g., carrier waves through air). The transmission medium 204 may carry control and addressing signals from the detection logic to the sensors 205 and may carry detected values from the sensors 205 to the detection logic 206.

In an embodiment, the plurality of sensors 205 are a linear array of six or more sensors, for example, twenty-two or more sensors such as thirty-six sensors, or even more. If there are thirty-six sensors, the transmission medium 205 may include six input wires and six output wires, and the detection logic 206 may be configured to control the multiplexing of detected values along the output wires. For example, a detection cycle may be divided into six sub-cycles, where, for each sub-cycle, six detected values are received on six respective output lines. Thus, after six sub-cycles the values detected by all 36 sensors have been read. For each sub-cycle, the detection logic may use one of the six input lines to select six of the thirty-six sensors. In an aspect of the invention, a detection cycle has a frequency greater than fifteen hertz, for example, forty hertz or greater such as two hundred hertz, or even more. Accordingly, in such aspects where signals detected by thirty-six sensors are being multiplexed during six sub-cycles, the frequency of the sub-cycles may be greater than ninety hertz, for example, two hundred forty hertz or greater such as 1.2 kilohertz or even greater.

The detection logic 206 also may include signal processing logic to process the signals carrying the values received over transmission medium 204. For example, the signal process logic may include noise filtering logic, analog-to-digital conversion logic and other logic to convert the raw detected values into suitable form to be input to visualization component 106. Detection logic 206 may include any of the logic described in the Son PCT application.

As is shown in FIG. 2, the probe 202 and sensors 205 of the detection component 102 may be inserted into a human 208 or another organism. For example, the probe may be inserted through the nasal cavity 219 into the upper GI tract such that at least a portion of the probe 202 resides in the pharynx 210, the UES 212, the esophagus 214, the LES 216 and the stomach 218. Although FIG. 2 illustrates the probe inserted within the upper GI tract, the probe may be inserted in any of a variety of combination of organs, including tubular organs. For example, the probe 202 may be inserted in the duodenum, the small bowel, the bile duct, the colon, the Sphincter of Oddi, the urethra, the anus or the rectum.

Each sensor may be arranged to be spaced a predefined distance from a nearest one or more other sensors. Optionally, the spacing between each pair of sensors may be configured to be approximately the same. In an aspect of the invention, this same spacing may be three centimeters or less, for example, two centimeters or less such as one centimeter, or even less than one centimeter.

The sensors 205 may be configured to sense any of a variety of physical properties, for example, pressure, pH, temperature, voltage, tissue impedance, another physical property or any combination thereof.

Figure 3:
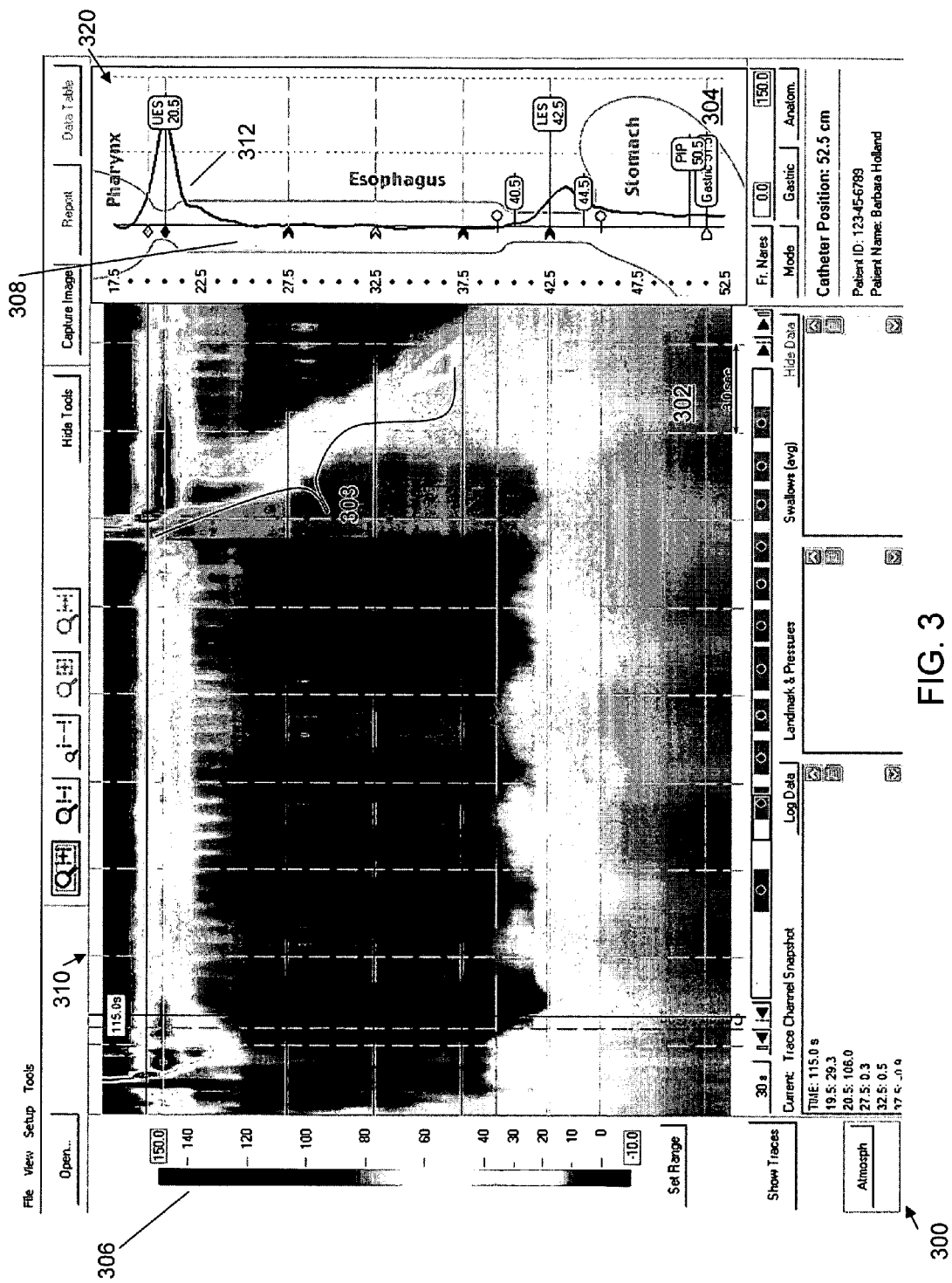
FIG. 3 is a screenshot illustrating an example of a user interface display at a first point in time.

FIG. 3 is a screenshot illustrating an example of a user interface display 300, which may be provided by user interface 112. In this example, display 300 includes two displays for providing visual representations of pressure data to a user: temporal display 310 and snapshot display 320. Temporal display 310 may be a display having both a temporal dimension and a spatial dimension, and may contain a temporal representation, e.g., contour plot 302. Snapshot display 320 may be a display having spatial dimension, including a spatial visual axis, and may contain a spatial representation, e.g., profile plot 304 that illustrates pressure data (or other data) for a particular time, as opposed to over a period of time.

Contour plot 302 may be displayed on a left-side of temporal display 310. Contour plot 302 may represent to a user pressure data derived from pressure information measured by sensors (e.g., sensors 205) at a plurality of positions over time. In the example shown in FIG. 3, the plurality of positions for which the pressure data are represented to the user may represent positions within the esophageal tract at which sensors 205 are positioned. In this example, the horizontal dimension of contour plot 302 represents time and the vertical dimension represents a first spatial dimension (e.g., within an organism).

In contour plot 302, the pressure data may be represented by multiple tones corresponding to multiple ranges of pressure values that correspond to the pressure data. Each tone may represent a respective range of pressure values. The size (i.e., granularity) of the ranges may be uniform. The uniform granularity of the ranges of pressure values may vary, and may be so fine that the spectrum of tones seems continuous to the human eye. A tone may be any suitable visual differentiating characteristic. For example, each tone may be any of a variety of colors or shades of gray, or any other suitable visually differentiating characteristic. Display 300 may include a tone bar 306, for example, on the left side of contour plot 302. The tone bar may be a legend which maps a tone to a corresponding pressure range. For example, in some embodiments, the color blue may represent a low pressure range and the color red may represent a high pressure range. Tone bar 306 may assist users in determining the pressure values corresponding to tones displayed in contour plot 302.

Some aspects of the invention may provide for multiple tone ranges for pressure data represented in different regions of temporal representation 310. A control may allow for switching between the ranges. For example, the user may define one range to be in a relatively small range of pressure values to provide higher pressure resolution in a pressure range of interest. Another range may be defined for another region, e.g., a wide pressure interval for viewing a region with a wider range of pressure values at a lower pressure resolution.

Any suitable type of temporal representation may be used in place of contour plot 302 for viewing pressure values measured at a plurality of measurement positions over time. For example, the temporal representation may be a three-dimensional plot, a shaded contour plot, a mesh plot, or any other suitable type of plot.

Display 300 may include a profile plot 304 in snapshot display 320. Profile plot 304 may represent pressure data derived from pressure information measured at a plurality of measurement positions at a particular time. In FIG. 3, this pressure data is represented using a profile line trace 312, in which pressure values of the pressure data are represented by the horizontal offset of the profile line trace 312 from a vertical spatial axis 306. Snapshot display 320 may contain any suitable spatial representation in place of profile plot 304 that represents pressure data derived from pressure information measured at a plurality of measurement positions at a particular time, e.g., tones corresponding to pressure, bars having lengths corresponding to pressures, etc.

Snapshot display 320 may have displayed along the vertical spatial dimension a representation of a region within an organism where sensors are located to collect data. For example, profile plot 304 may include a representation of the esophageal tract. In FIG. 3, the pharynx, esophagus and stomach are represented along the vertical spatial dimension, centered along axis 308. The locations of these organs with respect to the vertical spatial dimension may correspond with their respective positions in an actual esophageal tract. In some embodiments, profile plot 304 may include tags that represent other features of the esophageal track. For example, tags may be included at locations within snapshot display 320 to represent positions of the UES, the LES, and the PIP.

In some embodiments of the invention, the temporal representation 302 may move horizontally along the temporal dimension to illustrate the passage of time during the temporal interval in which the pressure values being represented were measured. For example, the right-most edge of temporal representation 302 may correspond to a latest time of the times during the temporal interval being represented in temporal representation 302, and the left-most edge may represent an earliest time. To illustrate the passage of time during the temporal interval, the temporal representation 302 may continually shift to the left across the screen, thus allowing a user to view a representation of pressures measured in the esophagus over time. This continuous shift to the left enables users to see changes in pressure (if any) over time at the positions being represented, and may enable users to see the occurrence of an event (e.g., a peristaltic wave) in which the pressure information was measured (e.g., in the upper GI tract).

For example, in temporal representation 302, a visual representation of the pressures in the GI tract during a swallow may be displayed. A user may determine that a swallow has occurred by viewing the portions of temporal representation 302 that contains tones indicative of a high pressure wave. For example, portion 303 of temporal representation 302 may represent a swallow (i.e., peristaltic wave). This swallow begins at the portion of temporal representation 302 that is in the same vertical location as the UES marker in pressure profile plot 304. As time moves forward (toward the right in the temporal dimension, the representation itself moving left), the representation of the swallow can be seen progressing down the esophagus to the LES.

It should be appreciated that the "time" represented by a location along a temporal dimension of temporal display 310 (and other temporal displays discussed herein) does not necessarily correspond to a precise instant of time, but may correspond to a discrete, atomic, sub-interval of time within the interval of time being represented. By "atomic", what is meant is that the sub-interval represented may be the smallest unit interval of time being represented. For example, the smallest units of time being represented may be milliseconds. The pressure data (or other data) represented at a particular temporal location in a temporal display may be data detected within the atomic subinterval (i.e., time) represented by the location. Moreover, the pressure information (represented by the pressure data) detected at different positions during this sub-interval may have actually been detected at different times during the sub-interval. For example, pressure information may be measured, for two or more different sensors, at different times within a sub-interval represented by a temporal location in a temporal display.

Further, in some embodiments, at least some of the temporal locations may represent a time at which no pressure information was actually measured. The pressure values displayed at these locations may be values interpolated or otherwise determined based on pressure values of adjacent locations or other locations in the temporal display. Pressure values may be interpolated in a temporal and/or spatial dimension. In some embodiments, the pressure data may be made quasi-continuous in the temporal and/or spatial dimension even though pressures may be detected at discrete times and/or positions. Pressure data may be made quasi-continuous by including interpolated pressure values in the pressure data. A quasi-continuous visual representation (e.g., having smooth changes) may be provided based on quasi-continuous pressure data. Any suitable visual representation discussed below may be quasi-continuous. Viewing a quasi-continuous visual representation may facilitate locating aspects of a region (e.g., the UES, LES, and PIP) and placing markers at locations, and interpreting the visual representation.

Figure 4:
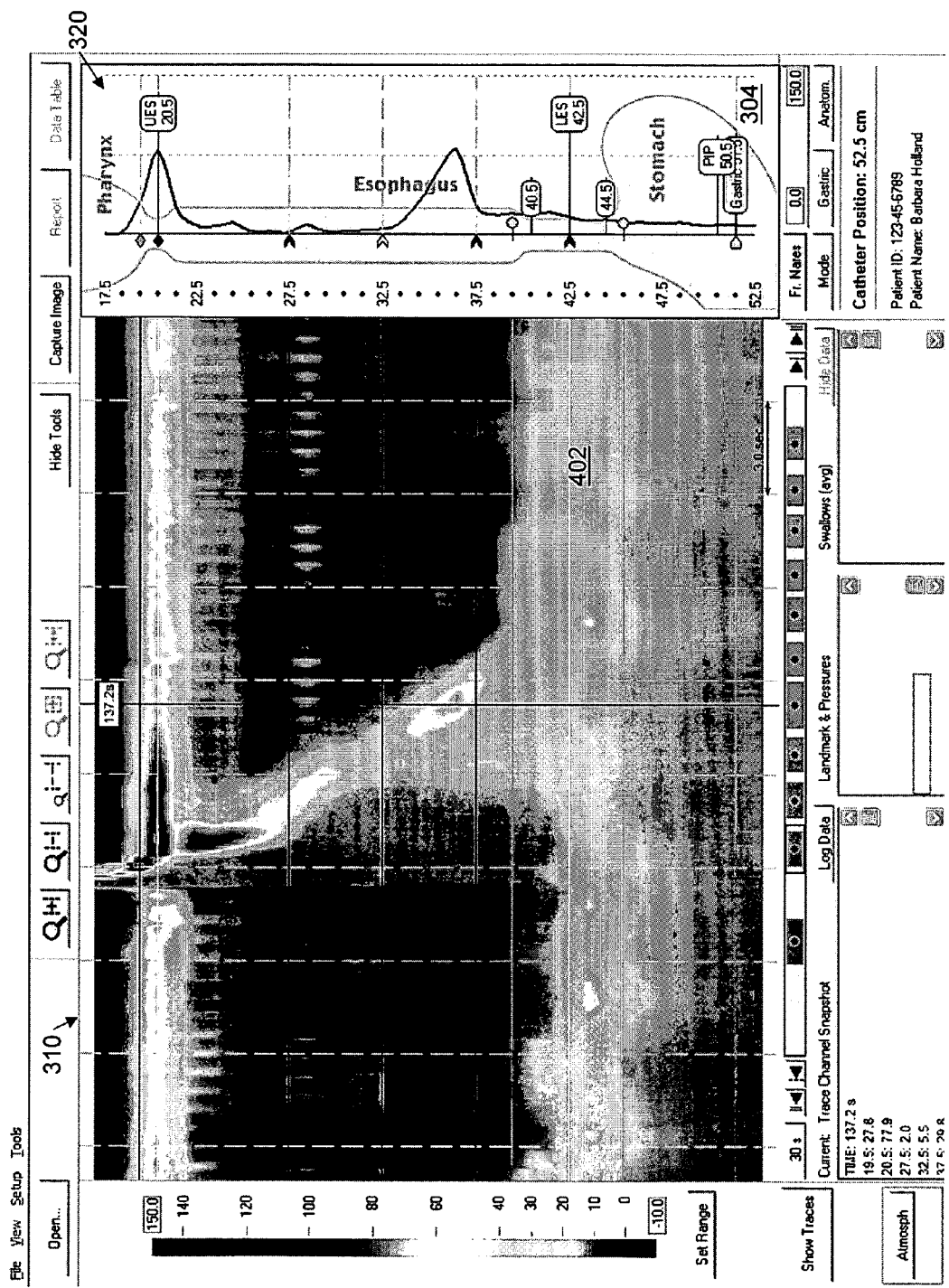
FIG. 4 is a screenshot illustrating an example of a user interface display at a second point in time.

FIG. 4 is a screenshot illustrating an example of a temporal representation 402, similar to representation 302, but shifted in time (to the left). Temporal representation 402 may be what a user would see several seconds after viewing the temporal representation 302 illustrated in FIG. 3. Thus, FIGS. 3 and 4 illustrate a temporal representation progressing horizontally to the left as time moves forward.

Figure 5:
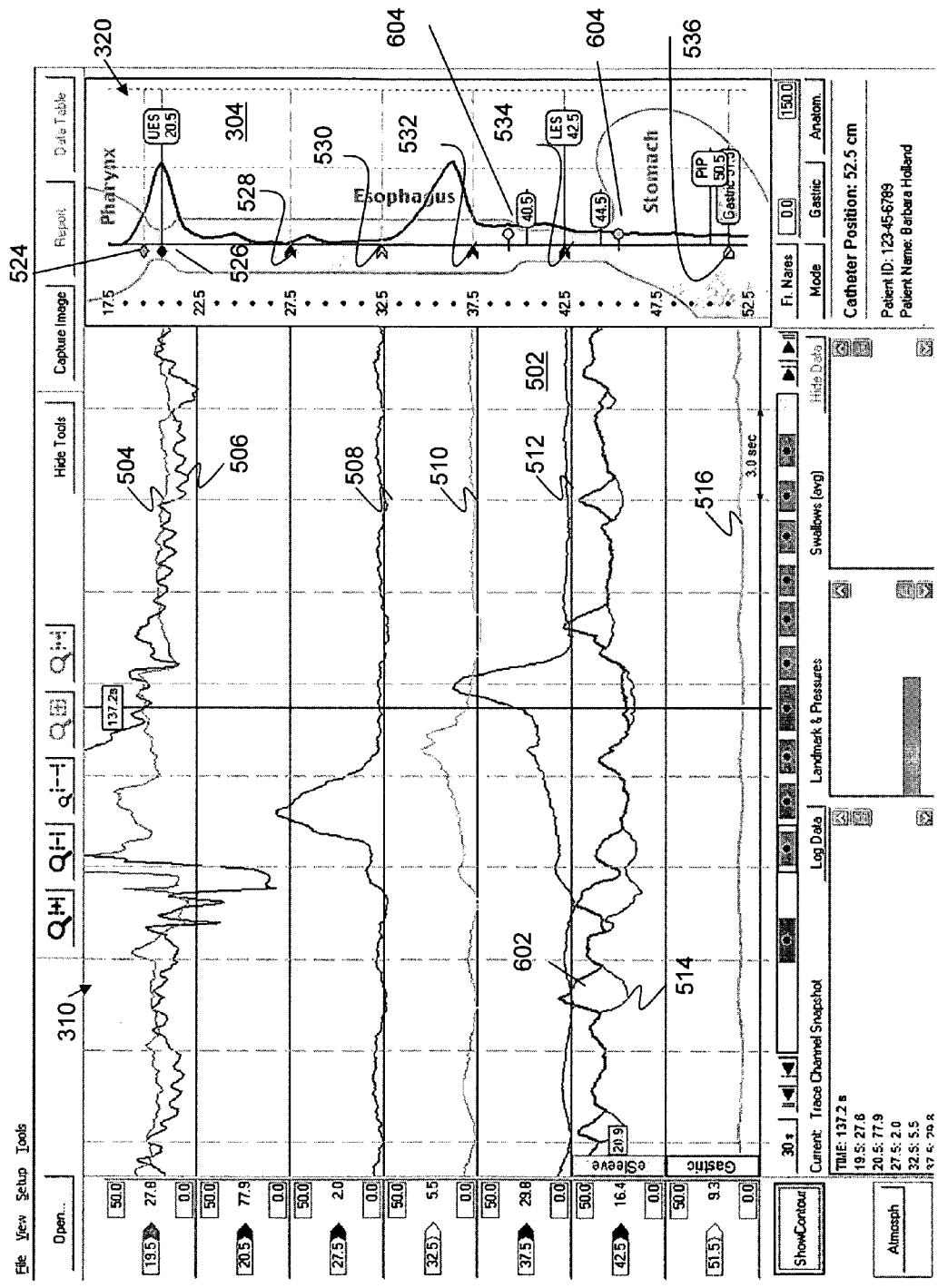
FIG. 5 is a screenshot illustrating an example of a user interface display showing an alternative representation.

FIG. 5 illustrates an example of a temporal display 310 representing pressure information measured over time in the upper GI tract. Temporal display 310 may represent the same pressure data as shown in FIG. 4. FIG. 5 shows in temporal display 310 line trace representation 502, which may include several line traces. Each line trace 504, 506, 508, 510, 512, 514 and 516 may represent pressure data corresponding to pressure information detected by a sensor at a particular position within an esophagus. Each position may correspond to a respective marker 526, 528, 530, 532, 534, and 536 of snapshot plot 320, each of which may be selected and movable by a user. At each particular time along the temporal dimension, the height of a line trace above a baseline location represents a value of the pressure information measured at the position (within the esophageal track) represented by the line trace at the particular time.

The elements displayed in FIGS. 3-5 and described above are presented to provide context for, and a better understanding of, embodiments of the invention described herein. These embodiments will now be described.

It may be desirable to determine characteristics of the organism using system 100 and provide a visual representation to a user. For example, it may be desirable to determine the maximum pressure in a sphincter region of an organism at a particular time. The maximum pressure may be used to determine a barrier property of a sphincter muscle. One known way of determining the maximum pressure in a sphincter region of an organism is to use a Dent sleeve.

A Dent sleeve is an apparatus that uses perfuse water pressure sensing technology, and incorporates a sleeve along a length (e.g., 5 cm) of a catheter pressure probe. A Dent sleeve is configured such that the maximum pressure along the length of the sleeve is converted into an electrical signal representing the maximum pressure for a measurement interval. A Dent sleeve may be used, for example, to characterize the barrier properties of sphincter muscles by placing the Dent sleeve such that it spans a sphincter region. It may be difficult to position the Dent sleeve precisely within the sphincter region. If the Dent sleeve is not positioned precisely, the sleeve may output an electrical signal that is not representative of the maximum pressure of a sphincter region as intended, but rather of another muscle, for example.

In one aspect of the invention, the maximum sphincter pressure may be determined using system 100, as will now be described in relation to FIGS. 6 and 7.

Figure 6:
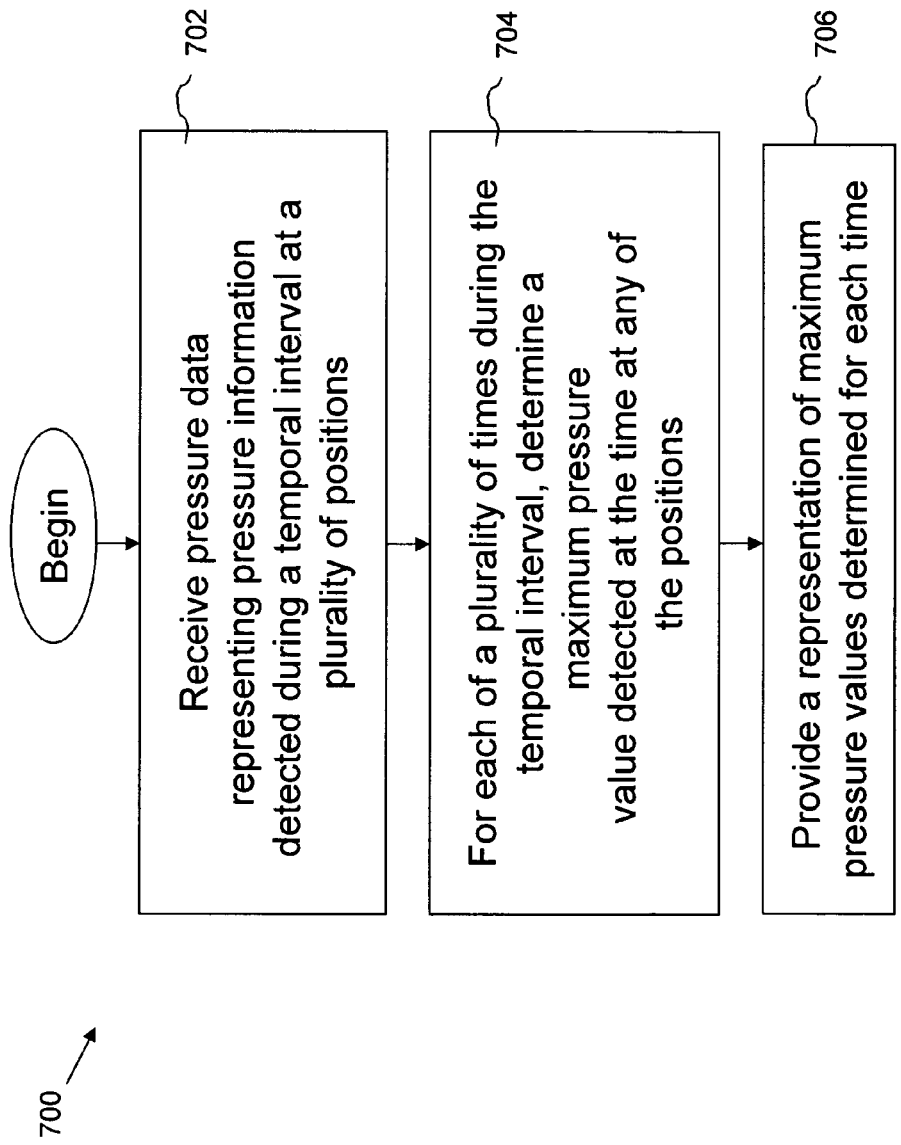
FIG. 6 is a flowchart illustrating an example of a method of processing sphincter data.

FIG. 6 is a flowchart illustrating an example of a method 700 of determining maximum pressure values detected within a region (e.g., a sphincter region) of an organism during a temporal interval. Method 700 may be implemented at least partially using maximum pressure module 114. In one embodiment of the invention, an eSleeve may be provided using the method shown in FIG. 6. As its name implies, unlike the Dent sleeve, an "eSleeve" is not an actual physical sleeve separate from the probe (e.g., catheter) that measures the pressure information and determines a maximum pressure value. Rather, pressure information is included within the pressure information collected by the probe, and the maximum pressure value may be determined by components (e.g., 106) of system 100.

In act 702, the system may receive sphincter pressure data representing pressure information measured during a temporal interval at a plurality of positions within a sphincter. The sphincter pressure data may be received in any suitable way via any suitable transmission media. Any suitable component and/or module may receive the sphincter pressure data, e.g., maximum pressure module 114 of visualization component 106.

In act 704, for each of a plurality of times during the temporal interval, a maximum sphincter pressure value detected at any of the positions at the time may be determined, for example, by comparing the pressure values within a specified region. The pressure values may be compared using maximum pressure module 114.

In act 706, a visual representation of the maximum pressure values determined for each time may be provided, for example, in eSleeve trace 602 described below in relation to FIG. 7. It is to be appreciated that any suitable representation of maximum pressure values may be used, e.g., a bar graph, a line trace, a contour plot, other representations or any suitable combination of the foregoing.

Figure 7:
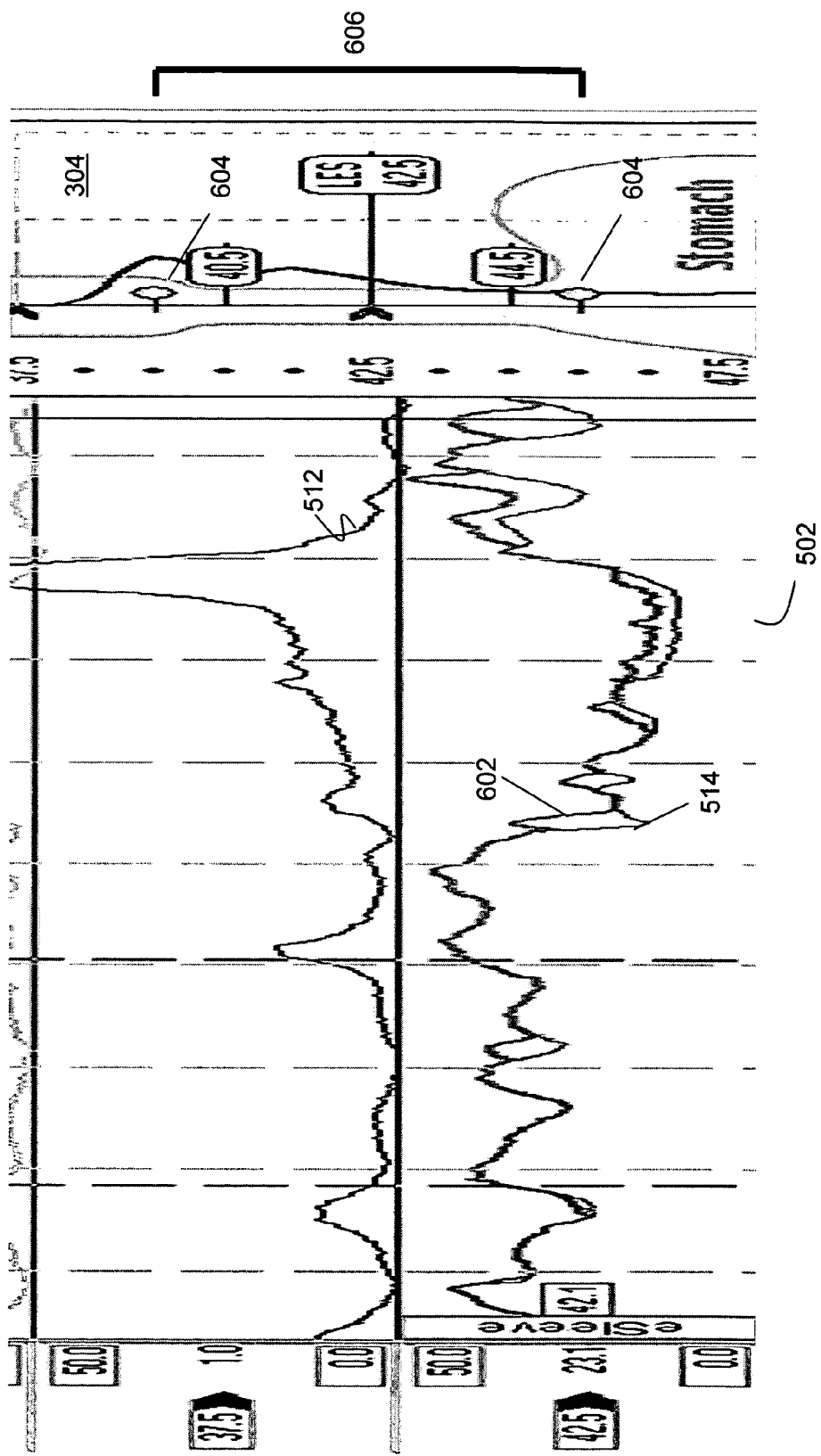
FIG. 7 is a portion of a screenshot illustrating an example of a line trace corresponding to maximum pressure values in a sphincter region.

FIG. 7 is a portion of a screenshot illustrating a portion of profile plot 304 and a portion of line trace representation 502. Within the portion of profile plot 304, the eSleeve boundary 606 may be demarcated by markers 604. Each of eSleeve boundary markers 604 may be configured to be movable by a user along a spatial baseline (e.g., axis) of pressure profile plot 304. This ability to move the boundary markers may enable the user to selectively delimit the eSleeve boundary 606, and place the eSleeve boundary 606 precisely on the region of interest (e.g., a sphincter) and avoid inclusion of other anatomical regions.

One or more guidelines (not shown) may be provided within a temporal representation (e.g., a contour plot and/or line trace representation 502) for determining the location for eSleeve boundary marker 604. A guideline may be provided at a location on the temporal representation which corresponds to the position within the region represented by eSleeve boundary marker 604. As a user moves eSleeve boundary marker 604 along the spatial dimension of pressure profile plot 304, the guideline may move accordingly along the spatial dimension of the temporal representation. The guideline may enable a user to determine the location for eSleeve boundary marker 604 that corresponds with the position of an appropriate region of interest (e.g., a sphincter region).

Line trace representation 502 also includes an eSleeve trace 602. The eSleeve trace 602 represents the maximum pressure in the sphincter region 606 over the time illustrated in line trace representation 502. For each time, the maximum pressure within the sphincter region 606 may be determined (e.g., by maximum pressure module 114) by comparing a plurality of values of the pressure information measured within this region (e.g., a sphincter) at the time.

Method 700 may include additional acts. Further, some or all of the acts may be performed concurrently to other acts, and need not necessarily be performed in the order described above.

Having thus described a method 700 of determining maximum pressure values detected within a region (e.g., a sphincter region) of an organism during a temporal interval, a method 900 of representing pressure data measured over time within an organism will now be described.

Figure 8:
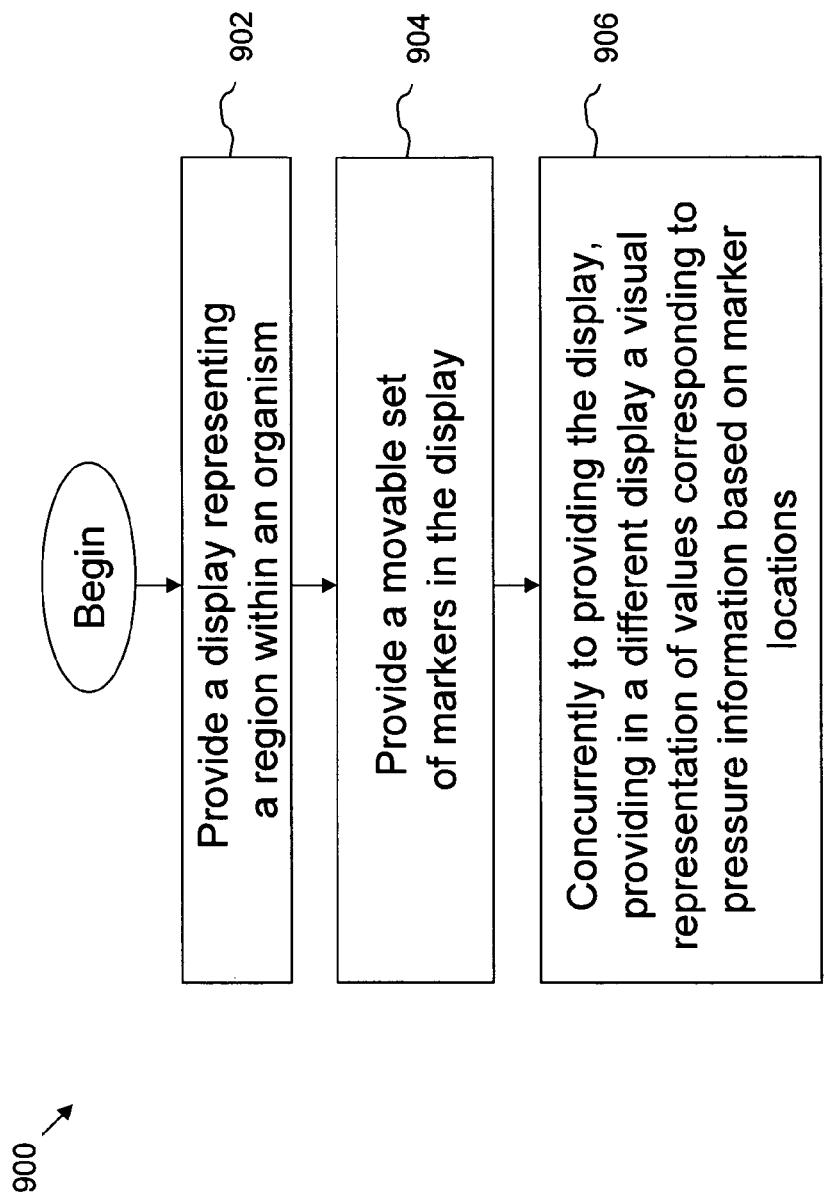
FIG. 8 is a flowchart illustrating an example of a method of visually representing pressure data.

FIG. 8 is a flowchart illustrating an example of a method 900 of representing pressure data measured over time within an organism to assist a user in locating a PIP, LES, UES or other area of interest within the esophageal tract. Method 900 may be implemented at least partially using region of interest location module 116.

Method 900 may enable a user to determine, based on pressure values measured at a plurality of positions in an organism over time, one or more aspects of an organism. For example, the user may be enabled to locate the UES, LES the PIP or other area of interest in the upper GI tract. Visual representations of pressure information corresponding to positions represented by a user-movable set of markers may be provided that enable a user to visually determine a position of such a region of interest. By moving the movable set of markers, the user may control the visual representation of pressure data, which may facilitate finding the position of the region of interest.

In act 902, the system 100 may provide a first display representing a first region within an organism may be provided.

In act 904, a movable set of markers may be provided in the first display, for example as shown in FIGS. 9A and 9B.

FIGS. 9A and 9B depict one way in which an area within an organism may be represented by moving a movable set of markers. FIG. 9A shows a movable set of markers 810 that includes three markers spaced a fixed distance apart from one another: first marker 802, second marker 804, and third marker 806. Any suitable number of markers may be included in the movable set of markers, e.g., greater or less than three. As used herein, the term "fixed distance apart" means that the distance between any two markers in the movable set of markers does not change as any one marker of the set is moved, e.g., in the process of locating an aspect of the organism. That is, the markers are only moveable as a set—when one marker of the set is moved, the other markers are moved a same distance in a same direction.

In the embodiment shown in FIGS. 9A and 9B, the movable set of markers is located in profile plot 304, on which the location of each marker along the vertical dimension represents a position along a spatial dimension within the organism. It should be appreciated that the movable set of markers could be located in any of a variety of other suitable locations indicative of position within the organism.

In act 906, and concurrently to providing the first display, a visual representation of values corresponding to pressure information may be provided in the second display. For each marker in the movable set of markers, there may be provided in temporal display 310 a visual representation of values corresponding to pressure information measured over time at the respective position along the spatial dimension of the organism represented by each marker. As shown in FIGS. 9A and 9B, three line traces 812, 814, and 816 may be provided in display 310 for markers 802, 804, and 806, respectively, shown in display 320. Each line trace represents values corresponding to pressure information measured over time at the position represented by the corresponding marker. By viewing and comparing the line traces, a user may determine the position of an area of interest within the organism, for example, as described below in relation to FIG. 10.

Method 900 may include additional acts. Further, some or all of the acts may be performed concurrently to other acts, and need not necessarily be performed in the order described above.

Figure 10:
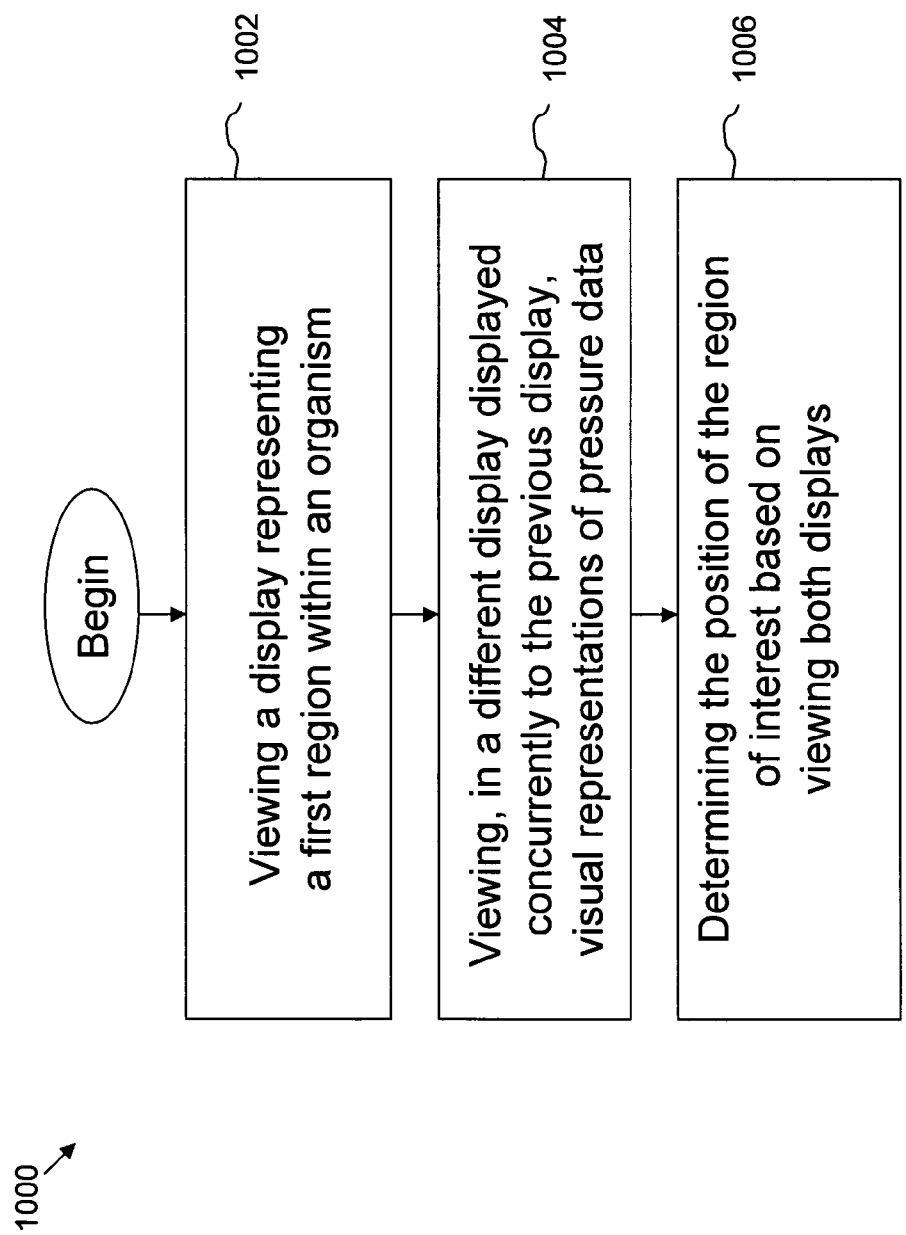
FIG. 10 is a flowchart illustrating an example of a method of locating a region of interest within an organism.

FIG. 10 is a flowchart illustrating an example of a method 1000 of locating a region of interest within an organism, e.g., the PIP, LES, or UES within the esophageal tract. In act 1002, a user may view a first display representing a first region within an organism. For example, a user may view profile plot 302 as illustrated in FIG. 9A.

In act 1004, the user may view, in a second display displayed concurrently to the first display, visual representations of pressure data. For example, a user may view temporal display 310 as illustrated in FIG. 9A.

In act 1006, the user may determine the position of the region of interest based on the viewing of the first and second displays. Any suitable criteria may be used to determine the position of the region of interest, and criteria for determining the position may depend on the type of region, e.g., UES, PIP, LES, etc.

In one aspect of the invention shown in FIG. 9A, the user may desire to locate the PIP within the upper GI tract of a human body. By selecting and moving tag 820 or any of markers 802, 804 and 806 (which are a fixed distance apart from one another), the user may move the movable set of markers to a first location along the vertical dimension of profile plot 304. In response to the moving of the movable set of markers to the first location, each of line traces 812, 814, and 816 may be updated accordingly.

As shown in FIG. 9A, each of the line traces 812, 814, and 816 are substantially periodic and substantially in phase with one another. Line traces 812, 814, and 816 may be substantially periodic because the pressures in the esophageal change in response to respiration, which may be substantially periodic. A phase shift between two periodic waveforms having the same period may correspond to the temporal shift between the waveforms' respective maxima. As used herein, waveforms are said to be "in phase" if the phase shift between the waveforms is negligible. Because line traces 812, 814, and 816 are substantially in phase in FIG. 9A, a user may determine that each of the positions represented by the respective markers is on the same side of the PIP.

If a waveform is inverted, the inverted waveform may be phase-shifted by 180° with respect to the original waveform. As discussed above, the PIP (the pressure inversion point) is named as such because it is a point along the length of the upper GI tract (typically within, but sometimes distal to, the LES) where the pressure associated with respiration inverts. The PIP is also known as the RIP (respiratory inversion point), and as used herein the two terms PIP and RIP have equivalent meanings.

Line traces corresponding to pressures located below the PIP may be phase-shifted by approximately 180° with respect to line traces corresponding to pressures located above the PIP. A user may determine the position of the PIP by moving the movable set of markers until there is approximately a 180° phase shift between two line traces shown in display 310. The user, upon viewing two line traces which are phase shifted by approximately 180°, may determine the PIP to be at a position between the positions represented by the markers that correspond to the two line traces.

For example, the line traces 812', 814', and 816' may be displayed as a result of a user moving markers 802, 804, and 806, respectively to the locations shown in FIG. 9B. In FIG. 9B, first line trace 812' and third line trace 816' are approximately 180° phase-shifted from one another because the maximum of first line trace 812' is shifted a time interval of approximately half of the period of the waveforms from the maximum of third line trace 816'. Upon viewing the approximately 180° phase shift between first line trace 812' and third line trace 816', the user may determine that the PIP is between the positions within the esophageal tract represented by first marker 802 and third marker 806 in FIG. 9B.

A movable set of markers may be used to determine the position of another aspect of an organism, such as the UES or LES. In one embodiment, a sphincter may be located using a movable set of markers and viewing the corresponding line traces as discussed above. However, instead of looking for a phase shift between different line traces, a sphincter may be located by viewing the pressure values indicated by the line traces.

A line trace of representing pressure information at a position within the upper GI tract may have periodic minima (i.e., "respiratory cycle minima") resulting from a respiratory cycle. The position of the LES may be defined as the position in the esophagus having a maximum value for respiratory cycle minima. For example, in temporal display 310 of FIG. 9A (assuming for the sake of illustration that the pressure information being represented corresponds to an LES region, not a PIP region as indicated in snapshot display 320), the minima of line trace 816 are greater than the minima of line trace 814. If, upon moving the movable set of markers to several different locations, a user does not observe a line trace with greater minima that those of line trace 816, the position of the LES may be determined to be the position within the esophageal tract corresponding to marker 806.

As another example, the position of the UES may be defined as the position in the upper GI tract, e.g., during a temporal interval during which a swallow or other event is not occurring. The position of the UES may be found using the movable set of markers as well. The UES may not display respiratory cycle variations—so the sphincter center may be defined as the position of maximum mean pressure. The movable set of markers may be used to locate such a position.

As discussed above, interpolated pressure values may be generated. Interpolated pressure values may represent pressure information for positions within the upper GI tract between positions of sensors 205. Providing pressure data that includes interpolated pressure values may enable the display of a visual representation (e.g., a temporal representation and/or snapshot display) of pressure information which is quasi-continuous. A quasi-continuous representation of pressure information may allow a user to determine a precise location for a marker (e.g., markers 528, 530, and 532) with respect to the spatial dimension (e.g., of snapshot display 320 and/or temporal display 310). Thus, providing interpolated pressure values may allow for more precise determination of the position of an aspect of an organism than would otherwise be possible (i.e., with pressure data having "discrete" spatial resolution). This aspect of the invention is not limited to finding an aspect of an organism, but may also be applied to other embodiments, e.g., determining a location for an eSleeve boundary marker 604.

Method 900 may include additional acts. Further, some or all of the acts described above with respect to FIG. 10 may be performed concurrently to other acts, and need not necessarily be performed in the order described above.

Having thus described a system and methods for representing pressure data and locating a region of interest using a movable set of markers with respect to FIGS. 8-10, another aspect of the invention will now be described with respect to FIGS. 11-13.

In another aspect of the invention, one or more sets of markers on a temporal display may be used to illustrate the occurrence of an event within an organism. One or more markers may be displayed on a temporal representation in temporal display 310. A set of such markers may correspond with a position within a region of interest and may define a temporal sub-interval. The temporal sub-interval defined by the set of markers may correspond to an event represented by pressure information. In some embodiments, the markers of the set of markers are movable by a user in a temporal dimension of the temporal representation. For example, a user may move one or more of the set of markers so that the temporal sub-interval defined by the set of markers more accurately corresponds with the corresponding event.

Figure 11:
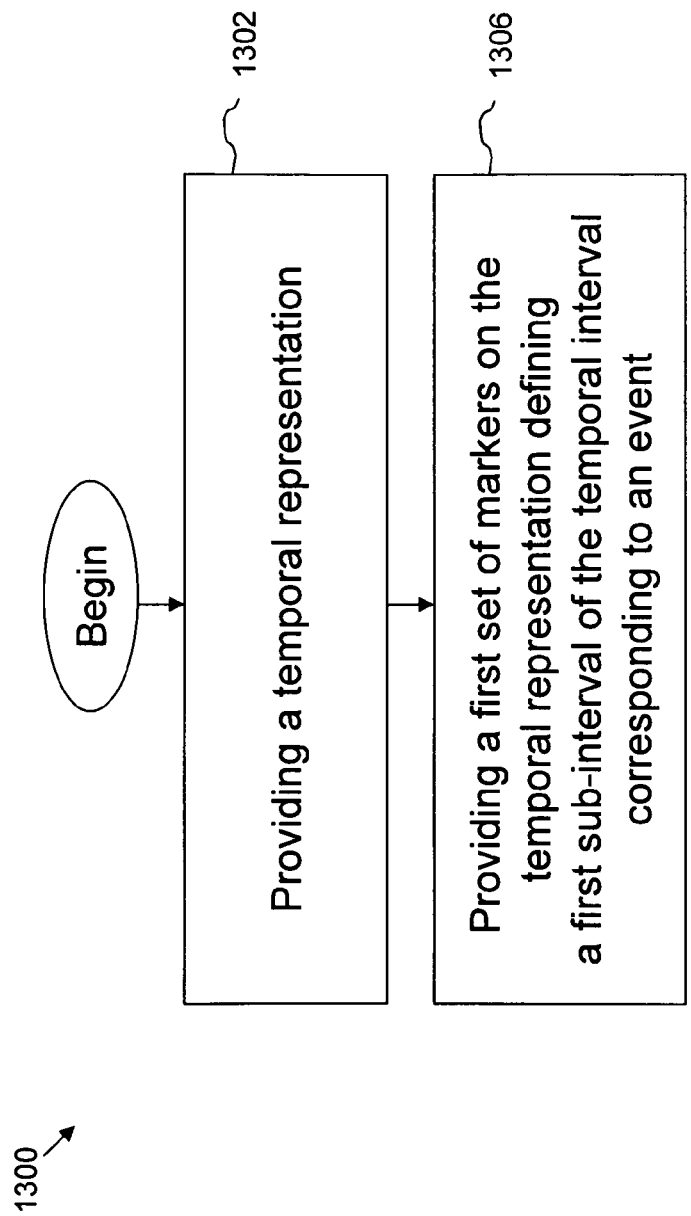
FIG. 11 is a flowchart illustrating an example of a method of visually representing pressure information using markers.

FIG. 11 is a flowchart illustrating an example of a method 1300 of visually representing pressure information. Method 1300 may be implemented at least partially using location marker providing module 118. In act 1302, the system may provide a temporal representation. FIG. 12 is a screenshot illustrating an example of a portion of a contour plot 1110 which may be displayed in temporal display 310. Contour plot 1110 may have displayed thereon a set of markers 1102, and may include other sets of markers (not shown). Markers 1102 may correspond to a position within the upper GI tract represented by guideline 1104, and may define a temporal sub-interval 1106 corresponding to a peristaltic wave.

Figure 12:
FIG. 12 is a portion of a screenshot illustrating an example of sets of markers on a contour plot.
Figure 13:
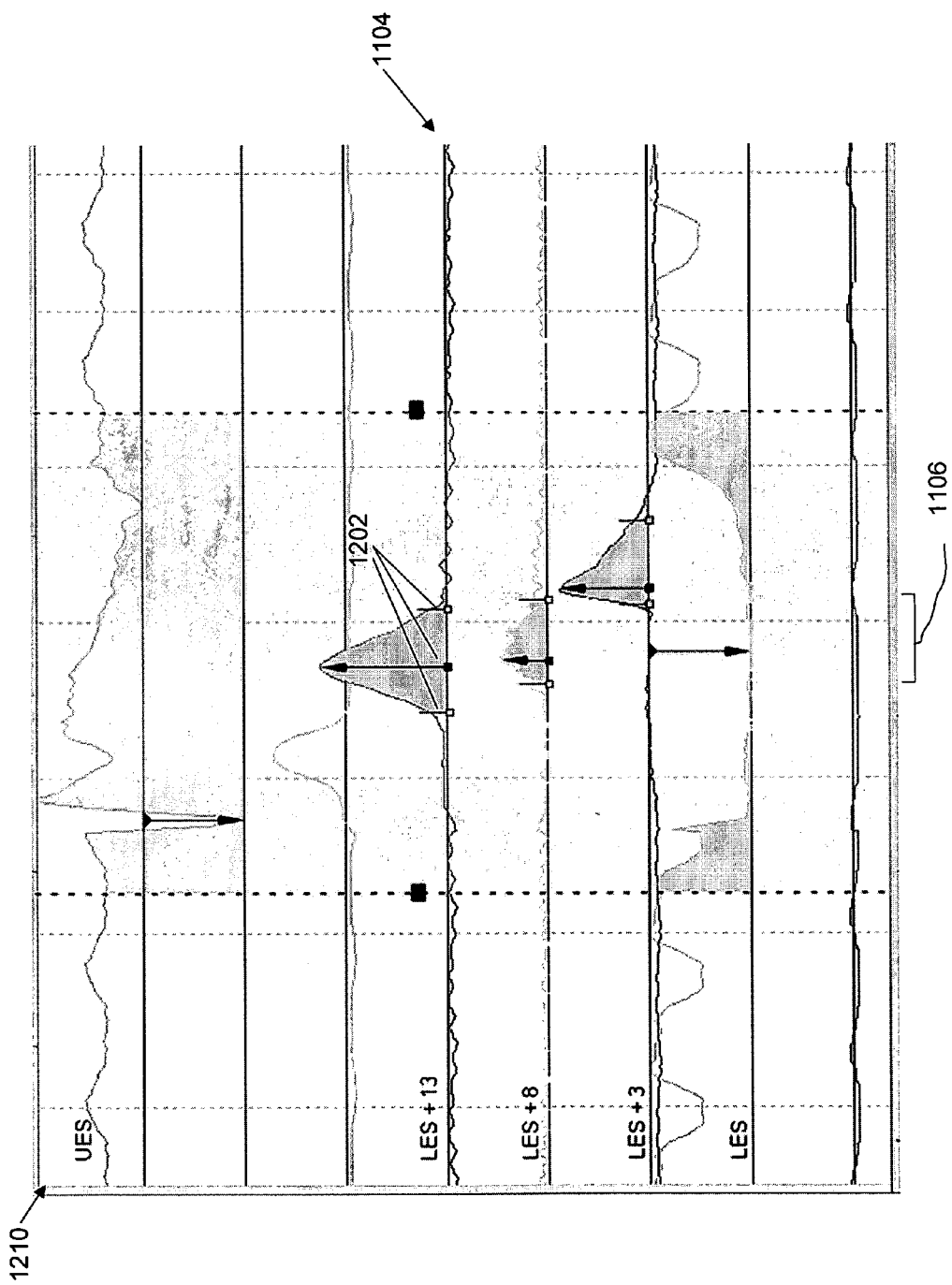
FIG. 13 is a portion of a screenshot illustrating an example of sets of markers on line traces.

In FIG. 12, the set of markers 1102 includes three markers, but it is to be appreciated that any suitable number of markers greater or less than three may be used. The leftmost marker of the set of markers 1102 may define the beginning of temporal sub-interval 1106. The rightmost marker of the set of markers 1102 may define the end of temporal sub-interval 1106. The middle marker of the set of markers 1102 may indicate a time within temporal sub-interval 1106 at which a maximum pressure was measured for temporal sub-interval 1106.

In some situations, the location of one or more markers of the set of markers 1102 may be controlled by system 100, for example, by visualization component 106. Visualization component 106 may be configured to apply one or more algorithms to determine points in time indicated by the markers based on one or more criteria. For example, the beginning of the temporal sub-interval may be determined based on a pressure value exceeding a threshold value, the end of the sub-interval may be determined based on a pressure value below a threshold value after the beginning, and the middle may be determined based on a maximum pressure value between the beginning and the end. Any suitable criteria may be used to determine points in time indicated by the markers.

In some situations, a user may move one or more of the markers to a location representing a different point in time, for example, horizontally along the temporal dimension of contour plot 1110. The user may do so to align the markers with points in time (e.g., defining a sub-interval) the user believes are associated with an event.

In some embodiments, visualization component 106 may first determine points in time associated with an event and position markers at the determined points in time. A user then may move one or more of the markers to more accurately correspond with points in time associated with an event.

As discussed above, the system 100 may provide for displaying different temporal representations that represent the same pressure data in different ways. For example, a contour plot and a line trace representation may represent the same pressure data. FIG. 13 is a screenshot illustrating an example of a line trace representation 1210 that represents the same pressure data as is represented by contour plot 1110 in FIG. 12. In this example, the peristaltic wave to which markers 1102 correspond at the position represented by guideline 1104 is represented by line trace representation 1210. A set of markers 1202 corresponding to the position represented by guideline 1104 define the temporal sub-interval 1106 corresponding to the peristaltic wave. In one example, user interface 112 enable a user to switch (i.e., toggle) between viewing contour plot 1110 and line trace representation 1120 in temporal display 310. Providing markers on a contour plot 1110 and/or a line trace representation 1120 to correspond with an event may assist a user in locating the occurrence of an event, and may facilitate diagnoses.

In act 1306, the system may provide a first set of markers on the temporal representation. Act 306 may be performed by location marker providing module 118, and may provide markers as discussed in the examples above. Method 1300 may include other acts. Further, some or all of the acts described above with respect to FIG. 11 may be performed concurrently to other acts, and need not necessarily be performed in the order described above.

In one aspect of the invention, the system 100 (e.g., visualization component 106 and/or other components) may determine a characteristic of an event occurring within subintervals defined by a plurality of sets of markers based on the locations corresponding to the sets of markers. For example, the system may calculate a peristaltic wave front velocity using the locations of the leftmost markers in two sets of markers. The peristaltic wave velocity may be determined as the difference between the respective positions represented by the two sets of markers divided by the difference in the points in time represented by two leftmost markers. As another example, the system may determine a sphincter relaxation pressure. One definition of the sphincter relaxation pressure may be the lowest average pressure for any three second period during a swallow event. However, other suitable definitions of sphincter relaxation pressure may also be used. If the sphincter relaxation pressure is to be determined using the above definition, the system 100 may provide user-movable guide for finding the three second period. Any suitable guide may be used, e.g., a box on the temporal representation a set of guidelines on the temporal representation.

Any of a variety of other suitable characteristics may be determined based on locations of markers.

Having thus described a system and methods for illustrating the occurrence of an event within an organism using one or more set of markers, another aspect of the invention will now be described with respect to FIGS. 14-16.

In one aspect of the invention, it may be desirable to visually represent pressure information by providing a user-movable temporal control. A representation of pressure data at one particular time may be provided based on the location of the movable temporal control, thus allowing a user to choose a time for which the pressure information is to be visually represented in snapshot display 320. For example, a movable temporal control provided in temporal display 310 may be moved by a user to a location along the temporal dimension of the temporal display corresponding to a particular time. Based on the location of the movable temporal control, the system may provide in snapshot display 320 a visual representation of pressure information measured by the plurality of sensors at the time indicated by the movable temporal control.

Figure 14:
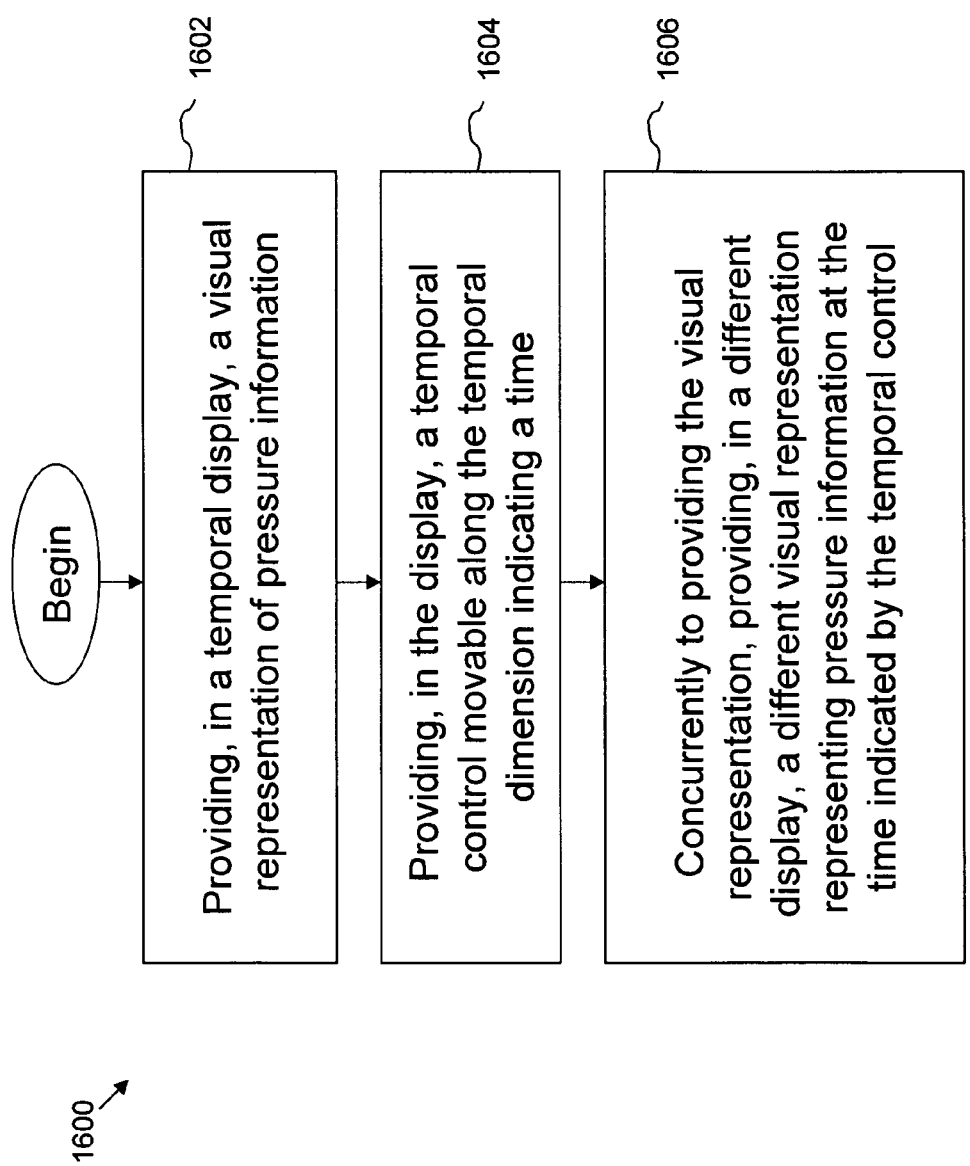
FIG. 14 is a flowchart illustrating of an example of a method of visually representing pressure information using a movable temporal marker.

FIG. 14 is a flowchart illustrating an example of a method 1600 of visually representing pressure information in a snapshot display corresponding to the location of a movable temporal control in a temporal display. Method 1600 may be implemented at least partially using temporal control module 120.

In act 1602, a first visual representation of pressure information may be provided in a temporal display. FIG. 15 is a screenshot illustrating an example of a temporal display 310 in which is displayed contour plot 1406 and a snapshot display 320 in which is displayed pressure line trace 1404.

In act 1604, the system may provide, in the first display, a temporal control movable along the temporal dimension. A temporal control 1402 is illustrated in temporal display 310 as a vertical line spanning the vertical dimension of display 310. However, it should be appreciated that any of a variety of other types of temporal controls may be used such as, for example, a control marker or a sliding bar. Temporal control 1402 may be movable horizontally by a user to select a temporal interval.

In act 1606, the system may provide, concurrently to, providing the first visual representation, in a second display, a second visual representation of pressure information measured by the plurality of sensors at the first time indicated by the temporal control. Snapshot display 1404 displays a pressure line trace representing pressure data measured at a plurality of positions measured at the time indicated by temporal control 1402.

Figure 15:
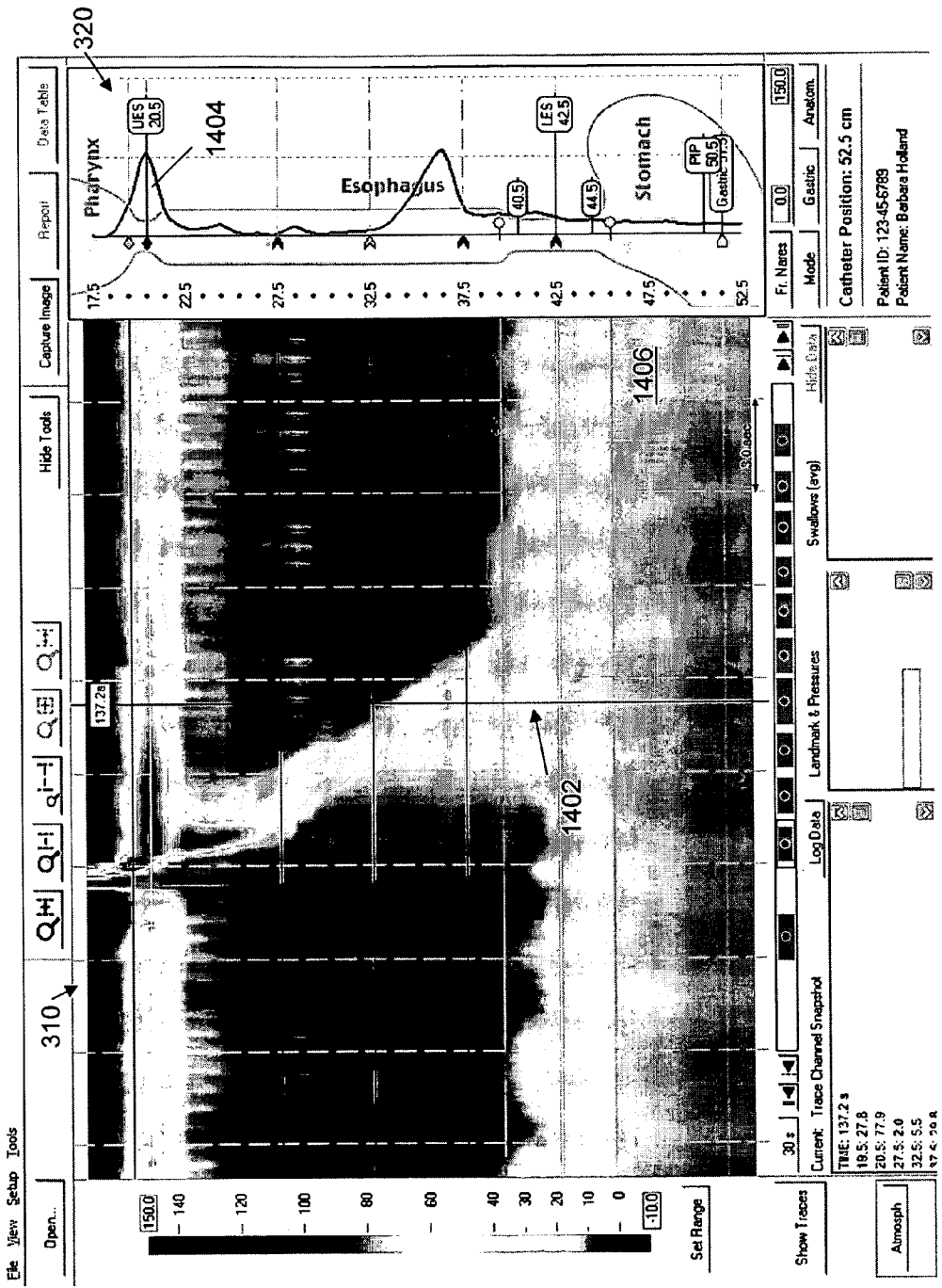
FIG. 15 is a portion of a screenshot illustrating an example of a movable temporal marker in a first location.
Figure 16:
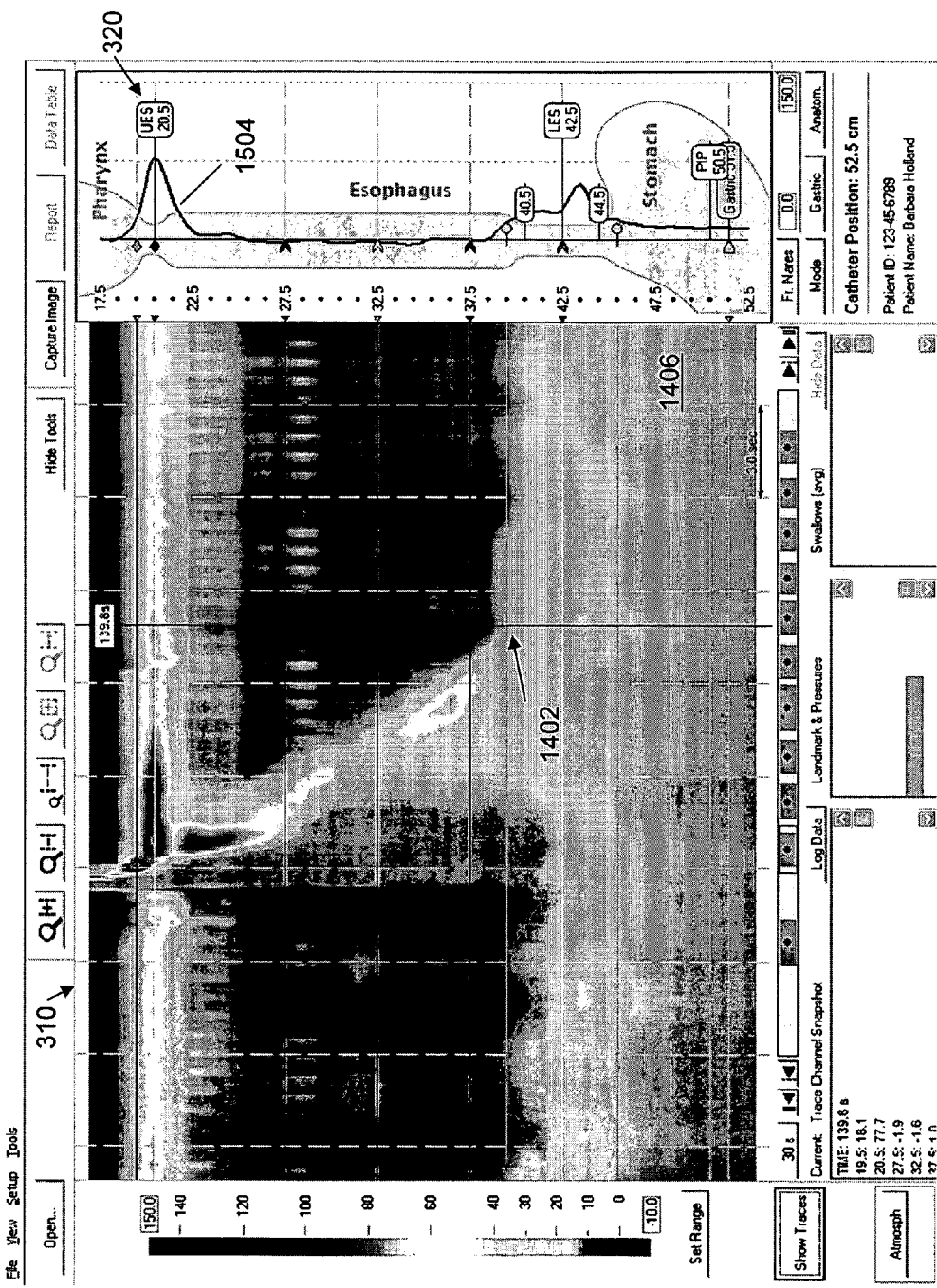
FIG. 16 is a portion of a screenshot illustrating an example of a movable temporal marker in a second location.

FIG. 16 is a screenshot illustrating the same contour plot 1406 as shown in FIG. 15; however, temporal control 1402 is in a different location and represents a different time than in FIG. 15. In this example, snapshot display 320 includes a different pressure line trace than that shown in FIG. 15. In FIG. 15, snapshot display 320 includes pressure line trace 1504 which represents pressure data measured at a plurality of positions measured at the time indicated by temporal control 1402 in FIG. 16.

Method 1600 may include additional acts. Further, some or all of the acts described above with respect to FIG. 14 may be performed concurrently to other acts, and need not necessarily be performed in the order described above.

Some aspects of the invention may process pressure data from the pharynx or more proximal sites to determine the occurrence of a voluntary initiation of a swallow. The initiation may be determined algorithmically by recognizing and analyzing abrupt rises and falls of pressure in regions above the UES such as the oropharynx or the base of tongue. Such detection may include identification of pressure changes of at least a certain magnitude that take place over no more than a certain number of seconds. This aspect of the invention may be useful in determining initiation of swallows to identify in a clinical study data record, and in determination of unprovoked (or spontaneous) swallows. The aspect may eliminate the need for a dedicated swallow transducer (typically a microphone type device), which is required in known systems.

Some aspects of the invention may include comparative sphincter position identification algorithms. These algorithms may compare the relative properties of pressure information measured at adjacent positions (e.g., by adjacent sensors) within an organism. The adjacent channels may correspond to a region in which a sphincter is located. The display locations may correspond to actual positions at which pressure was measured or to locations for which interpolated data has been estimated. Such interpolation may enable the representation of a spatially continuous relationship of pressure and time in a temporal display such that sphincter positions (e.g., as identified by the following algorithms) may be determined using an arbitrarily small spatial quantization.

Aspects of the invention are not limited to the following techniques for locating sphincter positions and other phenomena, as other techniques may be used.

Example methods:
 a. LES Method #1: Position where the respiratory cycle minimum pressure is a maximum. Pressure information detected at adjacent positions may be compared and the position at which the respiratory cycle minimum pressure is a maximum identified.
 b. LES Method #2: Position where the respiratory cycle mean pressure is a maximum. Pressure information detected at adjacent positions may be compared and the position at which the respiratory cycle mean pressure is a maximum identified.

c. LES Method #3: Position where the end expiratory phase of the respiratory cycle is a minimum is a maximum. Pressure information detected at adjacent positions may be compared and the position at which the respiratory cycle minimum is a maximum identified.

d. LES Method #4: Positions extracted from the curve of the position of maximum pressure as described in Method #8 below. Such positions may include the spatial average, median, the most proximal, or most distal points of the curve, or some combination thereof.

e. UES Method: Position where the pressure within the adjacent channel region is a maximum.

Some aspects of the invention may implement additional methods. Such methods may compute various parameters from sphincter pressure data:

a. Minimum Pressure: Finds the minimum pressure or filtered minimum pressure over a period of time (e.g., represented by a link trace) at a specific position. Embodiments include computing and reporting the average (evenly or unevenly weighted) of the lowest pressures including n % of the record during the observation period, where n may be fixed or specified by the user. Another embodiment includes taking an average of respiratory cycle minima during a time period.

b. Mean Pressure: Finds the mean pressure over a period of time at a particular position.

c. Maximum Pressure: Finds the maximum pressure or filtered maximum pressure over a period of time at a particular position. Embodiments include computing and reporting the average of the highest pressures including n % of the record during the time period where n may be fixed or specified by the user. Another embodiment includes taking an average of respiratory cycle maxima during the time period.

Another aspect of the invention may effect a trace sub-display (e.g., a pop-up display) layered on the contour plot main display, which may be used for fine adjustment of a pressure wave or sphincter feature markers. In an embodiment of this method, pointers in the line trace and the contour modes are graphically similar to assist in correlation between the modes. In another embodiment, the sub-display is vertically aligned with the corresponding location on the contour display and the pointers for both display modes are visible to further assist in the correlation.

In another aspect, quantitative data from temporal representation 310 may be displayed using a line drawing tool. Position, pressure, and time data from both the starting and end points of the line may be displayed. The tool also may support the computation of differential changes between the two points and global characteristics of the data enclosed by a geometric shape, e.g., defined by a diagonal line. The differential changes may include $\Delta s/\Delta t$ (wave velocity), $\Delta p/\Delta t$ (rate of change of pressure), $\Delta p/\Delta s$ (pressure gradient, where $\Delta$ is the difference in the respective variable evaluated at the endpoints, and s, t, and p are position, time and pressure, respectively). The global characteristics of the data enclosed by the geometric shape may include computed maximum pressure, minimum pressure, average pressure, and median pressure. The enclosed shape may be a rectangle, ellipse, another shape or a combination of the foregoing.

Yet another aspect of the invention may provide for the graphical selection of location for evaluation of the gastric or esophageal baseline pressures. The locations may be specified using a sliding pointer in the pressure profile, a sliding pointer at the margin or within the main contour display, a grid line within the main contour display, or any combination thereof. A baseline marker may be a horizontal line that is movable by a user vertically within temporal representation 310. Selection of a proper location for evaluation of the gastric and esophageal baselines may be important because the baseline values may be incorrect if evaluated at a location that is not far enough away from sphincter muscles or other sources of pressure. The method may provide a control for the normalization of the display data with respect to gastric, esophageal, or atmospheric pressure.

Evaluation of the acquired data relative to reference pressure levels may facilitate diagnostic evaluation of the esophagogastric junction (gastric baseline), peristaltic motor function within the esophagus (esophageal baseline), and the pharynx (atmospheric), for example. A property of a region within an organism may be determined by normalizing a region pressure to a baseline pressure. For example, a pressure barrier property of the LES region may be determined by subtracting a gastric baseline pressure value from a pressure associated with the LES.

A further aspect of the invention may provide for user-controlled display of motor function events using patient-collected data. For example, the system may display data of two classes: background and event. Background data may typically represent a quasi-steady-state condition such as is the case for a relaxed patient who is breathing normally. Event data may be derived from some transient event such as a swallow, cough, or spasm (including achalasia). The user may command a background and then command specific events that interrupt the background and display the corresponding transient event sequence. The background and/or events may reflect normal and/or abnormal (pathological) patient conditions.

In one embodiment of this aspect, the background and events are from the same patient or from patients with similar anatomy. The apparent position of the anatomy relative to the probe is adjusted in the data set if necessary such that the anatomical landmarks shown in the two classes of data are aligned or nearly aligned. In this case the event appears to happen approximately as it would under a continuously collected data set as the displayed sequence transitions from background to event.

In another embodiment of this aspect, the background data is repeated for every respiratory cycle or multiple respiratory cycles where the end of the background cycle is in respiratory phase with the beginning of the event. This further may make the transition from background to event appear to be continuous. This aspect of the invention may be useful for educational purposes in studying normal and abnormal patient conditions. A sequence of such conditions may be shown in an efficient manner and the salient spatio-temporal-manometric relationships identified and compared. This aspect also may be useful in training a user in operation of a manometric data collection system and related clinical procedures.

Methods described herein, acts thereof and various embodiments and variations of this method and these acts, individually or in combination, may be defined by computer-readable signals tangibly embodied on or more computer-readable media, for example, non-volatile recording media, integrated circuit memory elements, or a combination thereof. Computer readable media can be any available media that can be accessed by a computer. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, other types of volatile and non-volatile memory, any other medium which can be used to store the desired information and which can accessed by a computer, and any suitable combination of the foregoing.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, wireless media such as acoustic, RF, infrared and other wireless media, other types of communication media, and any suitable combination of the foregoing.

Computer-readable signals embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, or C++, Fortran, Pascal, Eiffel, Basic, COBOL, etc., or any of a variety of combinations thereof. The computer-readable media on which such instructions are embodied may reside on one or more of the components of any of systems described herein, may be distributed across one or more of such components, and may be in transition therebetween.

The computer-readable media may be transportable such that the instructions stored thereon can be loaded onto any computer system resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement the above-discussed aspects of the present invention.

Figure 17:
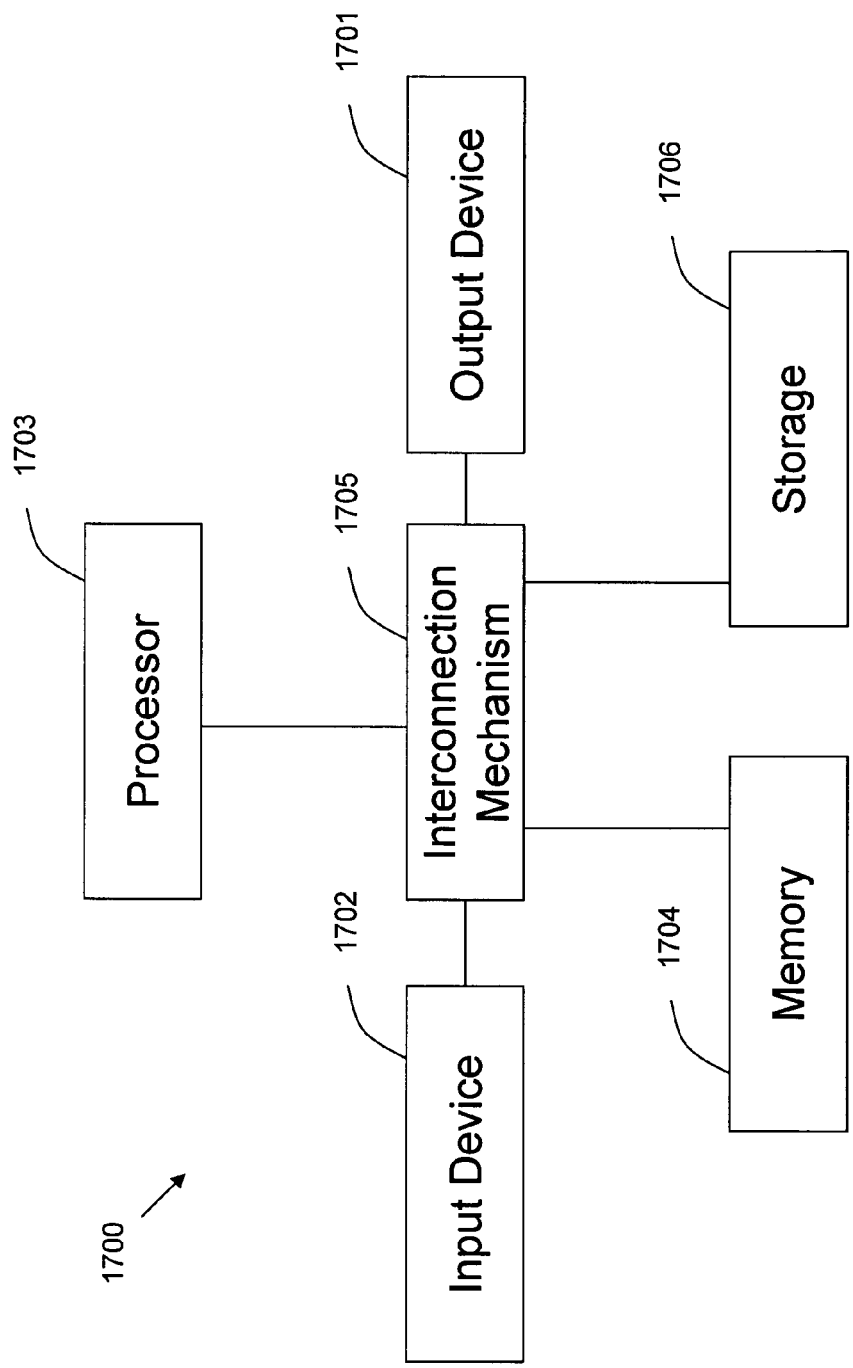
FIG. 17 is a block diagram illustrating an example of a computer system.
Figure 18:
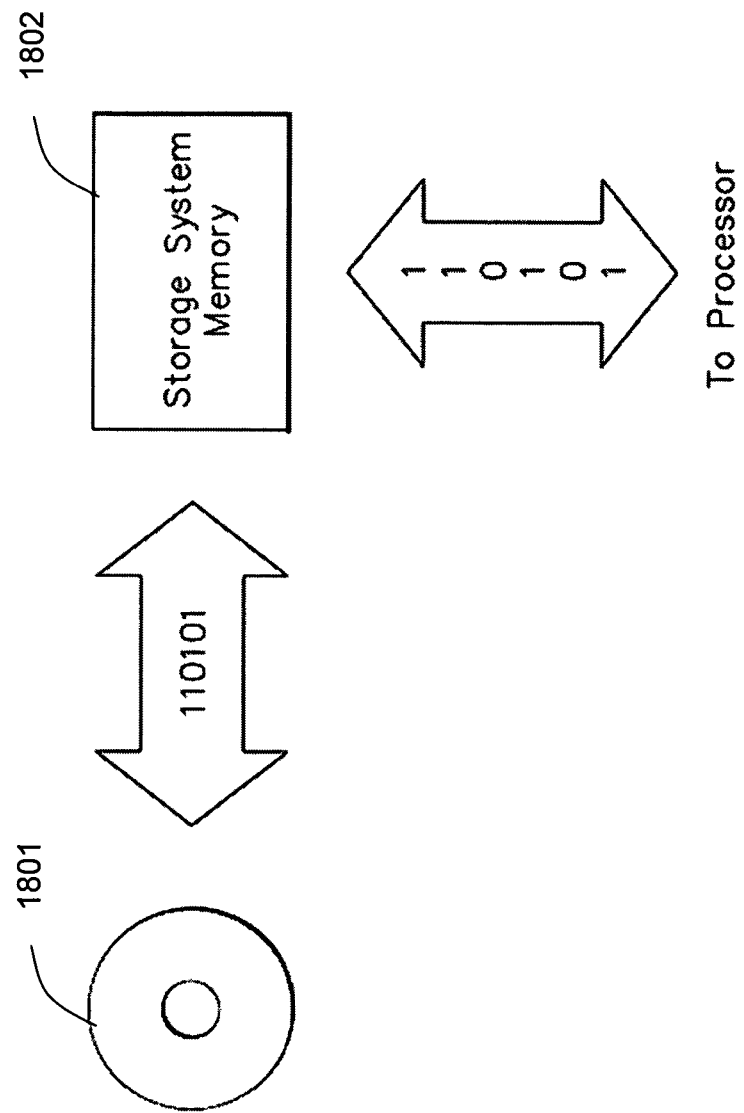
FIG. 18 is a diagram illustrating an example of data transfer.

It should be appreciated that any single component or collection of multiple components of a computer system, for example, the computer system described in relation to FIGS. 17 and 18 that perform the functions described herein can be generically considered as one or more controllers that control such functions. The one or more controllers can be implemented in numerous ways, such as with dedicated hardware and/or firmware, using a processor that is programmed using microcode or software to perform the functions recited above or any suitable combination of the foregoing.

Various embodiments according to the invention may be implemented on one or more computer systems. These computer systems, may be, for example, general-purpose computers such as those based on Intel PENTIUM-type processor, Motorola PowerPC, Sun UltraSPARC, Hewlett-Packard PA-RISC processors, or any other type of processor. It should be appreciated that one or more of any type computer system may be used to convert text to speech and/or edit speech on a portable audio device according to various embodiments of the invention. Further, the software design system may be located on a single computer or may be distributed among a plurality of computers attached by a communications network.

A general-purpose computer system according to one embodiment of the invention is configured to perform convert text to speech and/or edit speech on a portable audio device. It should be appreciated that the system may perform other functions and the invention is not limited to having any particular function or set of functions.

For example, various aspects of the invention may be implemented as specialized software executing in a general-purpose computer system 1700 such as that shown in FIG. 17. The computer system 1700 may include a processor 1703 connected to one or more memory devices 1704, such as a disk drive, memory, or other device for storing data. Memory 1704 is typically used for storing programs and data during operation of the computer system 1700. Components of computer system 1700 may be coupled by an interconnection mechanism 1705, which may include one or more busses (e.g., between components that are integrated within a same machine) and/or a network (e.g., between components that reside on separate discrete machines). The interconnection mechanism 1705 enables communications (e.g., data, instructions) to be exchanged between system components of system 1700. Computer system 1700 also includes one or more input devices 1702, for example, a keyboard, mouse, trackball, microphone, touch screen, and one or more output devices 1701, for example, a printing device, display screen, speaker. In addition, computer system 1700 may contain one or more interfaces (not shown) that connect computer system 1700 to a communication network (in addition or as an alternative to the interconnection mechanism 1705.

The storage system 1706, shown in greater detail in FIG. 18, typically includes a computer readable and writeable nonvolatile recording medium 1801 in which signals are stored that define a program to be executed by the processor or information stored on or in the medium 1801 to be processed by the program. The medium may, for example, be a disk or flash memory. Typically, in operation, the processor causes data to be read from the nonvolatile recording medium 1801 into another memory 1802 that allows for faster access to the information by the processor than does the medium 1801. This memory 1802 is typically a volatile, random access memory such as a dynamic random access memory (DRAM) or static memory (SRAM). It may be located in storage system 1706, as shown, or in memory system 1704, not shown. The processor 1703 generally manipulates the data within the integrated circuit memory 1704, 1802 and then copies the data to the medium 1801 after processing is completed. A variety of mechanisms are known for managing data movement between the medium 1801 and the integrated circuit memory element 1704, 1802, and the invention is not limited thereto. The invention is not limited to a particular memory system 1704 or storage system 1706.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

Although computer system 1700 is shown by way of example as one type of computer system upon which various aspects of the invention may be practiced, it should be appreciated that aspects of the invention are not limited to being implemented on the computer system as shown in FIG. 17.

Various aspects of the invention may be practiced on one or more computers having a different architecture or components that that shown in FIG. 17.

Computer system 1700 may be a general-purpose computer system that is programmable using a high-level computer programming language. Computer system 1700 may be also implemented using specially programmed, special purpose hardware. In computer system 1700, processor 1703 is typically a commercially available processor such as the well-known Pentium class processor available from the Intel Corporation. Many other processors are available. Such a processor usually executes an operating system which may be, for example, the Windows® 95, Windows® 98, Windows NT®, Windows® 2000 (Windows® ME) or Windows® XP operating systems available from Microsoft Corporation, MAC OS System X available from Apple Computer, the Solaris Operating System available from Sun Microsystems, UNIX available from various sources or Linux available from various sources. Many other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that the present invention is not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects of the invention may be performed on a client-server system that includes components distributed among one or more server systems that perform various functions according to various embodiments of the invention. These components may be executable, intermediate (e.g., IL) or interpreted (e.g., Java) code which communicate over a communication network (e.g., the Internet) using a communication protocol (e.g., TCP/IP).

It should be appreciated that the invention is not limited to executing on any particular system or group of systems. Also, it should be appreciated that the invention is not limited to any particular distributed architecture, network, or communication protocol.

Various embodiments of the present invention may be programmed using an object-oriented programming language, such as SmallTalk, Java, C++, Ada, J# (J-Sharp) or C# (C-Sharp). Other object-oriented programming languages may also be used. Alternatively, functional, scripting, and/or logical programming languages may be used. Various aspects of the invention may be implemented in a non-programmed environment (e.g., documents created in HTML, XML or other format that, when viewed in a window of a browser program, render aspects of a graphical-user interface (GUI) or perform other functions). Various aspects of the invention may be implemented as programmed or non-programmed elements, or any combination thereof.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any equivalent means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of processing pressure data comprising a plurality of pressure values indicative of pressure information measured by a plurality of sensors within a region of an organism and positioned along a length of the region, wherein the plurality of sensors are positioned at respective positions within a range of positions that extends along the length of the region, wherein endpoints of the range are defined by a first position of a first sensor of the plurality of sensors and a second position of a second sensor of the plurality of sensors, the method comprising acts of:
   (A) receiving pressure values from the plurality of sensors, each value indicating a measured pressure at a respective position within the region;
   (B) determining a sub-range of positions along the length of the region within the range of positions of the sensors, wherein the sub-range of positions comprises a plurality of the respective positions, and wherein determining the sub-range comprises receiving an input through a user interface component, the input specifying the sub-range of positions along the region;
   (C) for the sub-range of positions along the region, determining, from the pressure values, a maximum pressure value of a plurality of values corresponding to the plurality of the respective positions within the sub-range; and
   (D) displaying a maximum pressure plot concurrently showing maximum pressure values over time for the determined sub-range of positions.

2. The method of claim 1, wherein the act (C) comprises comparing pressure values indicative of pressure information measured by adjacent sensors of the plurality of sensors for the sub-range of positions along the region.

3. The method of claim 1, further comprising an act of:
   (E) determining a pressure barrier property of the sub-range of positions within the region at least partially by subtracting a gastric pressure value from the maximum pressure value.

4. The method of claim 1, wherein the pressure values represents pressure information measured during a first time, and wherein (C) comprises determining the maximum pressure value for the first time, and further comprising acts of:

(E) receiving further pressure values comprising a plurality of pressure values indicative of pressure information measured by the plurality of sensors during a second time; and (F) determining, from the further pressure values, a second maximum pressure value for the sub-range of positions along the region for the second time.

5. The method of claim 4, wherein (D) comprises displaying the maximum pressure value and the second maximum pressure value on the maximum pressure plot.

6. The method of claim 1, wherein the maximum pressure plot comprises a line trace representing the maximum pressure values at a plurality of times.

7. The method of claim 1, further comprising:
displaying a user interface component enabling the user to specify the sub-range of positions along the length of the region.

8. The method of claim 7, wherein displaying the user interface component comprises acts of:
providing a first display representing the region within the organism; and
providing at least one movable marker in the first display, the at least one movable marker being movable along a spatial dimension within the first display, the spatial dimension within the first display representing a spatial dimension along the region, the location of the at least one movable marker at least partially delimiting the sub-range of positions for which the maximum pressure value is determined in the act (C).

9. The method of claim 8, wherein the at least one movable marker comprises two moveable markers, respective locations of each of the two moveable markers delimiting the sub-range of positions.

10. A system for processing pressure data comprising a plurality of pressure values indicative of pressure information measured by a plurality of sensors within a region of an organism and positioned along a length of the region, the system comprising:
a catheter to which the plurality of sensors are attached at respective positions along the length of the region; and
a maximum pressure module operative to:
receive the pressure data;
display the pressure data and a user interface component enabling a user to specify a sub-range of positions along the length of the region;
receive an input through the user interface component, the input specifying the sub-range of positions along the region; and
determine from the pressure data, a maximum pressure value for the sub-range of positions along the region.

11. A non-transitory computer program product comprising:
a computer-readable medium; and
computer-readable signals, stored on the computer-readable medium, that define instructions that, as a result of being executed by a computer, control the computer to perform a method of processing pressure data comprising a plurality of pressure values indicative of pressure information measured by a plurality of sensors within a region of an organism and positioned along a length of the region, the plurality of sensors being positioned within a range of positions that extends along the length of the region, wherein endpoints of the range are defined by a first position of a first sensor of the plurality of sensors and a second position of a second sensor of the plurality of sensors, the method comprising acts of:
(A) receiving the pressure data;

(B) displaying the pressure data and a user interface component enabling a user to specify a sub-range of positions along the length of the region;

(C) receiving an input through the user interface component, the input specifying the sub-range of positions along the length of the region within the range of positions of the sensors, the sub-range of positions being smaller than the range of positions of the sensors; and (D) determining, from the pressure data, a maximum pressure value for the sub-range of positions along the region.

12. The method of claim 1, wherein:
the method further comprises (E) displaying the pressure values for a user; and
the pressure values are indicative of pressure information measured at a plurality of times comprising first and second times, and wherein (E) comprises concurrently displaying a representation of the pressure data for the first and second times.

13. The method of claim 12, wherein (E) comprises displaying a contour plot representing the pressure data for the plurality of times.

14. The method of claim 12, wherein the pressure data comprises interpolated pressure data representing pressure information for positions between adjacent sensors of the plurality of sensors, and wherein (E) comprises displaying the interpolated pressure data.

15. The method of claim 12, further comprising an act of:
(F) displaying, in a first display, at least one moveable marker that is moveable along a spatial dimension of the first display that corresponds to positions along the length of the region, wherein the location of the at least one movable marker at least partially delimits the sub-range of positions for which the maximum is determined in (C);
wherein the spatial dimension of the first display is aligned with a same spatial dimension of a representation of the pressure data-displayed in (E).

16. The method of claim 15, wherein (B) comprises receiving user input that moves the at least one moveable marker to delimit the sub-range.

17. The computer program product of claim 11, wherein the method further comprises an act of:
(E) determining a pressure barrier property of the sub-range of positions within the region at least partially by subtracting a gastric pressure value from the maximum pressure value.

18. The computer program product of claim 11, wherein the pressure data represents pressure information measured during a first time, and wherein (D) comprises determining the maximum pressure value for the first time, and the method further comprises acts of:
(E) receiving further pressure data comprising a plurality of pressure values indicative of pressure information measured by the plurality of sensors during a second time; and
(F) determining, from the further pressure data, a second maximum pressure value for the sub-range of positions of the region for the second time.

19. The computer program product of claim 18, wherein the method further comprises an act of:
(G) displaying a representation of maximum pressure values on a human-perceptible medium, the maximum pressure values comprising the maximum pressure value and the second maximum pressure value, the maximum pressure values corresponding to a plurality of times, the plurality of times comprising at least the first and the second times.

20. The computer program product of claim 19, wherein the representation comprises a line trace representing the maximum pressure values at the plurality of times.

21. The computer program product of claim 11, wherein the act (B) comprises:
   providing a first display representing the region within the organism; and
   providing at least one movable marker in the first display, the at least one movable marker being movable along a spatial dimension within the first display, the location of the at least one movable marker at least partially delimiting the sub-range of positions for which the maximum pressure value is determined in the act (B).

22. The computer program product of claim 21, wherein the at least one movable marker comprises two moveable markers, respective locations of each of the two moveable markers delimiting the sub-range of positions.

23. The computer program product of claim 11, wherein the pressure data is indicative of pressure information measured at a plurality of times, and wherein (B) comprises displaying a representation of the pressure data for the plurality of times.

24. The computer program product of claim 23, wherein (B) comprises displaying a contour plot representing the pressure data for the plurality of times.

25. The computer program product of claim 23, wherein the act (B) further comprises:
   displaying, in a first display, at least one moveable marker that is moveable along a spatial dimension of the first display that corresponds to positions along the length of the region, wherein the location of the at least one movable marker at least partially delimits the sub-range of positions for which the maximum is determined in (D);
   wherein the spatial dimension of the first display is aligned with a same spatial dimension of a representation of the pressure data-displayed in (B).

26. A method of processing pressure data comprising a plurality of pressure values indicative of pressure information measured by a plurality of sensors within a region of an organism, wherein the plurality of sensors are positioned at respective positions within a range of positions that extends along the length of the region, wherein endpoints of the range are defined by a first position of a first sensor of the plurality of sensors and second position of a second sensor of the plurality of sensors, the method comprising acts of:
   (A) receiving pressure values from the plurality of sensors, each value indicating a measured pressure at a respective position within the region during a first time;
   (B) determining a sub-range of positions along the length of the region within the range of positions of the sensors, wherein the sub-range of positions comprises a plurality of the respective positions, and wherein determining the sub-range comprises receiving an input through a user interface component, the input specifying the sub-range of positions along the region; and
   (C) determining, from the pressure values, a first maximum pressure value for the sub-range of positions along the region for a first time;
   (D) receiving further pressure values comprising a plurality of pressure values indicative of pressure information measured by the plurality of sensors during a second time;
   (E) determining, from the further pressure values, a second maximum pressure value for the sub-range of positions along the region for the second time; and
   (F) displaying, on a human-perceptible medium, a maximum pressure plot of maximum pressure values over time for the determined sub-range of positions, the maximum pressure plot concurrently showing the first maximum pressure value, the second maximum pressure value and other maximum pressure values determined for the sub-range of positions over time.

27. The method of claim 26, further comprising:
   displaying a user interface component enabling the user to specify the sub-range of positions along the length of the region.

28. The method of claim 27, wherein (B) the method further comprises:
   (G) displaying the pressure values for a user; and
   displaying, in connection with the pressure values, at least one moveable marker that is moveable along a spatial dimension that corresponds to a length of the region, wherein the location of the at least one movable marker at least partially delimits the sub-range of positions for which the maximum is determined in (C).

29. The method of claim 28, wherein the location of the at least one moveable marker along the spatial dimension is aligned with a location along the spatial dimension of a representation of the pressure data displayed in (G).

30. The method of claim 28, wherein the at least one movable marker comprises two moveable markers, respective locations of each of the two moveable markers delimiting the sub-range of positions.

31. The method of claim 28, wherein (B) comprises receiving user input that moves the at least one moveable marker to delimit the sub-range.

32. The method of claim 26, wherein the method further comprises (G) concurrently displaying the pressure data and the further pressure data.

33. The method of claim 32, wherein (G) comprises displaying a contour plot representing the pressure data and further pressure data.

34. The method of claim 33, wherein the maximum pressure plot is displayed in (F) in a location that is aligned with a temporal dimension of the pressure data and the further pressure data.

35. The method of claim 1, wherein the region comprises a tubular organ of the organism.

36. The method of claim 35, wherein the tubular organ is an esophagus of a human body.

37. The method of claim 36, wherein the sub-range corresponds to an esophageal sphincter of the human body.

38. The system of claim 10, wherein the region comprises a tubular organ of the organism.

39. The system of claim 38, wherein the tubular organ is an esophagus of a human body.

40. The system of claim 38, wherein the sub-range corresponds to an esophageal sphincter of the human body.

41. The system of claim 38, wherein each sensor of the plurality of sensors is spaced less than three centimeters apart from another sensor of the plurality of sensors.

42. The system of claim 41, wherein the plurality of sensors are positioned at approximately equal intervals.

43. The system of claim 10, wherein the plurality of sensors comprises solid-state sensors.

44. The system of claim 10, wherein the plurality of sensors are positioned within a range of positions that extends along the length of the region, wherein endpoints of the range are defined by a first position of a first sensor of the plurality of sensors and a second position of a second sensor of the plurality of sensors, wherein the sub-range is within the range of positions of the sensors and the sub-range is smaller than the range of positions of the sensors.

45. The computer program product of claim 11, wherein the region comprises a tubular organ of the organism.

46. The computer program product of claim 45, wherein the tubular organ is an esophagus of a human body.

47. The computer program product of claim 46, wherein the sub-range corresponds to an esophageal sphincter of the human body.

48. The method of claim 26, wherein the region comprises a tubular organ of the organism.

49. The method of claim 48, wherein the tubular organ is an esophagus of a human body and the sub-range corresponds to a region comprising an esophageal sphincter of the human body.

50. The method of claim 26, wherein the maximum pressure plot comprises a line trace representing the maximum pressure values determined for the sub-range of positions for a plurality of times.

51. The method of claim 48, wherein the tubular organ is an anorectum of a human body and the sub-range corresponds to a region comprising a sphincter.

* * * * *

UNITED STATES PATENT AND TRADEMARK OFFICE
CERTIFICATE OF CORRECTION

PATENT NO. : 8,790,275 B2
APPLICATION NO. : 11/129030
DATED : July 29, 2014
INVENTOR(S) : Thomas R. Parks et al.

Page 1 of 1

It is certified that error appears in the above-identified patent and that said Letters Patent is hereby corrected as shown below:

In the Claims:

At column 28, line 15, claim 28, "wherein (B) the method further comprises" should read --wherein the method further comprises--.

At column 28, line 35, claim 32, "wherein the method further comprises (G) concurrently…" should read --wherein the method further comprises concurrently…--.

Signed and Sealed this
Twenty-first Day of October, 2014

Michelle K. Lee
*Deputy Director of the United States Patent and Trademark Office*